(12) United States Patent
Kates

(10) Patent No.: US 7,343,751 B2
(45) Date of Patent: Mar. 18, 2008

(54) INTELLIGENT THERMOSTAT SYSTEM FOR LOAD MONITORING A REFRIGERANT-CYCLE APPARATUS

(76) Inventor: Lawrence Kates, 1111 Bayside Dr., Corona Del Mar, CA (US) 92625

( * ) Notice: Subject to any disclaimer, the term of this patent is extended or adjusted under 35 U.S.C. 154(b) by 0 days.

(21) Appl. No.: 11/417,609

(22) Filed: May 3, 2006

(65) Prior Publication Data
US 2006/0196197 A1 Sep. 7, 2006

Related U.S. Application Data

(60) Division of application No. 11/130,562, filed on May 17, 2005, which is a continuation of application No. 10/916,222, filed on Aug. 11, 2004.

(51) Int. Cl.
*G01K 13/00* (2006.01)
*F25B 41/00* (2006.01)
*G05D 23/00* (2006.01)

(52) U.S. Cl. .............................. 62/129; 62/208; 236/94
(58) Field of Classification Search .................. 62/126, 62/129, 208, 209; 236/94; 165/11.1; 700/276; 702/130
See application file for complete search history.

(56) References Cited

U.S. PATENT DOCUMENTS 2,804,839 A 9/1957 Hallinan
(Continued)

FOREIGN PATENT DOCUMENTS

EP 0346152 A2 12/1989
(Continued)

OTHER PUBLICATIONS

Nickles, Donald, "Broadband Communications Over Power Transmission Lines," A Guest Lecture From the Dr. Shreekanth Mandayam Engineering Frontiers Lecture Series, 21 pages.
(Continued)

*Primary Examiner*—Marc Norman
(74) *Attorney, Agent, or Firm*—Knobbe, Martens, Olson & Bear, LLP

(57) ABSTRACT

A real-time monitoring system that monitors various aspects of the operation of a refrigerant-cycle system is described. In one embodiment, the system includes a processor that measures power provided to the refrigerant-cycle system and that gathers data from one or more sensors and uses the sensor data to calculate a figure of merit related to the efficiency of the system. In one embodiment, the sensors include one or more of the following sensors: a suction line temperature sensor, a suction line pressure sensor, a suction line flow sensor, a hot gas line temperature sensor, a hot gas line pressure sensor, a hot gas line flow sensor, a liquid line temperature sensor, a liquid line pressure sensor, a liquid line flow sensor. In one embodiment, the sensors include one or more of an evaporator air temperature input sensor, an evaporator air temperature output sensor, an evaporator air flow sensor, an evaporator air humidity sensor, and a differential pressure sensor. In one embodiment, the sensors include one or more of a condenser air temperature input sensor, a condenser air temperature output sensor, and a condenser air flow sensor, an evaporator air humidity sensor. In one embodiment, the sensors include one or more of an ambient air sensor and an ambient humidity sensor.

38 Claims, 25 Drawing Sheets

U.S. PATENT DOCUMENTS

| | | | |
|---|---|---|---|
| 3,027,865 A | 4/1962 | Kautz et al. | |
| 4,146,085 A | 3/1979 | Wills | |
| 4,153,003 A | 5/1979 | Willis | |
| 4,296,727 A | 10/1981 | Bryan | |
| 4,325,223 A * | 4/1982 | Cantley | 62/126 |
| 4,346,755 A | 8/1982 | Alley et al. | |
| 4,390,058 A | 6/1983 | Otake et al. | |
| 4,415,896 A | 11/1983 | Allgood | |
| 4,463,574 A | 8/1984 | Spethmann et al. | |
| 4,653,285 A | 3/1987 | Pohl | |
| 4,685,615 A | 8/1987 | Hart | |
| 4,716,957 A | 1/1988 | Thompson et al. | |
| 4,831,833 A | 5/1989 | Duenes et al. | |
| 4,835,706 A | 5/1989 | Asahi | |
| 4,903,759 A | 2/1990 | Lapeyrouse | |
| 4,916,909 A | 4/1990 | Mathur et al. | |
| 4,918,690 A | 4/1990 | Markkula, Jr. et al. | |
| 5,005,365 A | 4/1991 | Lynch | |
| 5,039,009 A | 8/1991 | Baldwin et al. | |
| 5,083,438 A | 1/1992 | McMullin | |
| 5,255,977 A | 10/1993 | Eimer et al. | |
| 5,274,571 A | 12/1993 | Hesse et al. | |
| 5,289,362 A | 2/1994 | Liebl et al. | |
| 5,381,669 A | 1/1995 | Bahel et al. | |
| 5,432,500 A | 7/1995 | Scripps | |
| 5,515,267 A | 5/1996 | Alsenz | |
| 5,546,073 A | 8/1996 | Duff et al. | |
| 5,566,084 A | 10/1996 | Cmar | |
| 5,590,830 A | 1/1997 | Kettler et al. | |
| 5,623,834 A | 4/1997 | Bahel et al. | |
| 5,628,201 A | 5/1997 | Bahel et al. | |
| 5,682,949 A | 11/1997 | Ratcliffe et al. | |
| 5,684,463 A | 11/1997 | Diercks et al. | |
| 5,689,963 A | 11/1997 | Bahel et al. | |
| 5,718,822 A | 2/1998 | Richter | |
| 5,729,474 A | 3/1998 | Hildebrand et al. | |
| 5,805,856 A | 9/1998 | Hanson | |
| 5,873,257 A | 2/1999 | Peterson | |
| 5,924,486 A | 7/1999 | Ehlers et al. | |
| 6,006,142 A | 12/1999 | Seem et al. | |
| 6,070,110 A | 5/2000 | Shah et al. | |
| 6,110,260 A | 8/2000 | Kubokawa | |
| 6,190,442 B1 | 2/2001 | Redner | |
| 6,192,282 B1 | 2/2001 | Smith et al. | |
| 6,216,956 B1 | 4/2001 | Ehlers et al. | |
| 6,230,501 B1 | 5/2001 | Bailey et al. | |
| 6,385,510 B1 | 5/2002 | Hoog et al. | |
| 6,397,612 B1 | 6/2002 | Kernkamp et al. | |
| 6,408,228 B1 | 6/2002 | Seem et al. | |
| 6,412,293 B1 | 7/2002 | Pham et al. | |
| 6,454,177 B1 | 9/2002 | Sasao et al. | |
| 6,487,457 B1 | 11/2002 | Hull et al. | |
| 6,591,620 B2 | 7/2003 | Kikuchi et al. | |
| 6,622,926 B1 | 9/2003 | Sartain et al. | |
| 6,643,567 B2 | 11/2003 | Kolk et al. | |
| 6,708,083 B2 | 3/2004 | Orthlieb et al. | |
| 6,711,470 B1 | 3/2004 | Hartenstein et al. | |
| 6,775,995 B1 | 8/2004 | Bahel et al. | |
| 6,837,922 B2 | 1/2005 | Gorin | |
| 6,973,410 B2 | 12/2005 | Seigel | |
| 6,973,793 B2 | 12/2005 | Douglas et al. | |
| 7,114,343 B2 | 10/2006 | Kates | |
| 7,201,006 B2 | 4/2007 | Kates | |
| 7,244,294 B2 | 7/2007 | Kates | |
| 7,275,377 B2 | 10/2007 | Kates | |
| 2002/0016639 A1 | 2/2002 | Smith et al. | |
| 2002/0082747 A1 | 6/2002 | Kramer | |
| 2002/0152298 A1 | 10/2002 | Kikta et al. | |
| 2002/0193890 A1 | 12/2002 | Pouchak | |
| 2003/0050737 A1 | 3/2003 | Osann | |
| 2003/0051490 A1 | 3/2003 | Jayanth | |
| 2003/0078677 A1 | 4/2003 | Hull et al. | |
| 2003/0089493 A1 | 5/2003 | Takano et al. | |
| 2003/0150924 A1 | 8/2003 | Rosen | |
| 2003/0150926 A1 | 8/2003 | Rosen | |
| 2003/0171851 A1 | 9/2003 | Brickfield et al. | |
| 2003/0183085 A1 | 10/2003 | Alexander | |
| 2003/0199247 A1 | 10/2003 | Strierner | |
| 2003/0205143 A1 | 11/2003 | Cheng | |
| 2003/0216837 A1 | 11/2003 | Reich et al. | |
| 2003/0233172 A1 | 12/2003 | Granqvist et al. | |
| 2004/0059691 A1 | 3/2004 | Higgins | |
| 2004/0111186 A1 | 6/2004 | Rossi et al. | |
| 2004/0133314 A1 | 7/2004 | Ehlers et al. | |
| 2004/0261431 A1 | 12/2004 | Singh et al. | |
| 2005/0229612 A1 | 10/2005 | Hrejsa et al. | |
| 2005/0229777 A1 | 10/2005 | Brown et al. | |
| 2005/0235664 A1 | 10/2005 | Pham | |
| 2005/0251293 A1 | 11/2005 | Seigel | |
| 2006/0032245 A1 | 2/2006 | Kates | |
| 2006/0032246 A1 | 2/2006 | Kates | |
| 2006/0032247 A1 | 2/2006 | Kates | |
| 2006/0032248 A1 | 2/2006 | Kates | |
| 2006/0032379 A1 | 2/2006 | Kates | |
| 2006/0036349 A1 | 2/2006 | Kates | |
| 2006/0196196 A1 | 9/2006 | Kates | |
| 2006/0201168 A1 | 9/2006 | Kates | |

FOREIGN PATENT DOCUMENTS

| | | |
|---|---|---|
| EP | 0346152 A3 | 12/1989 |
| WO | WO 00-21047 A1 | 4/2000 |

OTHER PUBLICATIONS

Tamarkin, Tom D., "Automatic Meter Reading," Public Power magazine, vol. 50, No. 5, Sep.-Oct. 1992, http://www.energycite.com/amr.html, 6 pages.

"Case Studies: Automated Meter Reading and Load Shed System," http://group-alpha.com/CaseStudies2.html, 1 page.

"LIPA Launches Free, First-in-Nation Internet-Based Air Conditioner Control Program to Help LIPA and its Customers Conserve Electricity & Save Money," Apr. 19, 2001, http://www.lipower.org/newscenter/pr/2001/april19_01.html, 3 pages.

" Frequently Asked Questions," http://www.lipaedge.com/faq.asp, 5 pages.

"Advanced Utility Metering: Period of Performance," Subcontractor Report, National Renewable Energy Laboratory, Sep. 2003, 59 pages.

"About CABA: CABA eBulletin," http://www.caba.org/aboutus/ebulletin/issue17/domosys.html, 2 pages.

"The LS2000 Energy Management System," User Guide, http://www.surfnetworks.com/htmlmanuals/LonWorksEnergyManagement-LS2000-Load-Shed-System-by-Surf-Networks, Inc.html, 20 pages.

"Low-Cost Multi-Service Home Gateway Creates New Business Opportunities," Coactive Networks, Copyright 1998-1999, 7 pages.

Texas Instruments, Inc., Product cataog for "TRF6901 Single-Chip RF Transceiver," Copyright 2001-2003, 27 pages.

Texas Instruments, Inc., Mechanical Data for "PT (SPQFP-G48) Plastic Quad Flatpack," 2 pages.

Jeffus, Larry, "Refrigeration and Air Conditioning: An Introduction to HVAC/R," Section II, Chapter 4, pp. 176-201, Copyright 2004.

Jeffus, Larry, "Refrigeration and Air Conditioning: An Introduction to HVAC/R," Section II, Chapter 5, pp. 239-245, Copyright 2004.

Jeffus, Larry, "Refrigeration and Air Conditioning: An Introduction to HVAC/R," Section II, Chapter 6, p. 322, Copyright 2004.

Jeffus, Larry, "Refrigeration and Air Conditioning: An Introduction to HVAC/R," Section IV, Chapter 9, pp. 494-504, Copyright 2004.

Jeffus, Larry, "Refrigeration and Air Conditioning: An Introduction to HVAC/R," Appendix C, pp. 1060-1063, Copyright 2004.

Udelhoven, Darrell, "Optimizing Air Conditioning Efficiency Tune-Up Optimizing the Condenser Output, SEER, AIR, HVAC Industry," http://www.udarrell.com/air-conditioning-efficiency.html, 13 pages.

Udelhoven, Darrell, "Air Conditioning System Sizing for Optimal Efficiency," http://www.udarrell.com/airconditioning-sizing.html, 7 pages.

Udelhoven, Darrell, "Air Conditioner EER, SEER Ratings, BTUH Capacity Ratings, & Evaporator Heat Load," http://www.udarrell.com/air-conditioner-capacity-seer.html, 15 pages.

"Flow & Level Measurement: Mass Flowmeters," http://www.omega.com/literature/transactions/volume4/T9904-10-MASS.html, 19 pages.

"Cost Cutting Techniques Used by the Unscrupulous," http://www.kellyshvac.com/howto.html, 3 pages.

Office Action dated Nov. 9, 2005 from Related U.S. Appl. No. 11/130,871.

Office Action dated Jan. 18, 2006 from Related U.S. Appl. No. 11/130,871.

Office Action dated Jul. 27, 2006 from Related U.S. Appl. No. 11/130,871.

Notice of Allowance date Feb. 12, 2007 from Related U.S. Appl. No. 11/130,871.

Office Action dated May 4, 2005 from Related U.S. Appl. No. 10/916,223.

Office Action dated Oct. 27, 2005 from Related U.S. Appl. No. 10/916,223.

Office Action dated Apr. 19, 2006 from Related U.S. Appl. No. 10/916,223.

Office Action dated Nov. 16, 2006 from Related U.S. Appl. No. 10/916,223.

Notice of Allowance dated Jul. 25, 2007 from Related U.S. Appl. No. 10/916,223.

Office Action dated Nov. 8, 2005 from Related U.S. Appl. No. 10/916,222.

Office Action dated Jan. 6, 2006 from Related U.S. Appl. No. 10/916,222.

Office Action dated Jul. 11, 2006 from Related U.S. Appl. No. 10/916,222.

Office Action dated Jan. 23, 2007 from Related U.S. Appl. No. 10/916,222.

Notice of Allowance dated Jun. 11, 2007 from Related U.S. Appl. No. 10/916,222.

Notice of Allowance dated Aug. 7, 2007 from Related U.S. Appl. No. 10/916,222.

Office Action dated Jun. 27, 2007 from Related U.S. Appl. No. 11/417,557.

Office Action dated Nov. 9, 2005 from Related U.S. Appl. No. 11/130,601.

Office Action dated Jan. 18, 2006 from Related U.S. Appl. No. 11/130,601.

Notice of Allowance dated Jul. 13, 2006 from Related U.S. Appl. No. 11/130,601.

Office Action dated Jul. 11, 2007 from Related U.S. Appl. No. 11/417,701.

Office Action dated Nov. 9, 2005 from Related U.S. Appl. No. 11/130,562.

Office Action dated Jan. 6, 2006 from Related U.S. Appl. No. 11/130,562.

Office Action dated Jul. 11, 2006 from Related U.S. Appl. No. 11/130,562.

Office Action dated Feb. 1, 2007 from Related U.S. Appl. No. 11/130,562.

Office Action dated Mar. 30, 2006 from Related U.S. Appl. No. 11/130,569.

Office Action dated Nov. 14, 2006 from Related U.S. Appl. No. 11/130,569.

Notice of Allowance dated May 29, 2007 from Related U.S. Appl. No. 11/130,569.

Notice of Allowance dated Oct. 26, 2007 from Related U.S. Appl. No. 10/916,223.

Office Action dated Aug. 21, 2007 from Related U.S. Appl. No. 11/417,557.

Office Action dated Aug. 17, 2007 from Related U.S. Appl. No. 11/417,701.

Office Action dated Sep. 18, 2007 from Related U.S. Appl. No. 11/130,562.

* cited by examiner

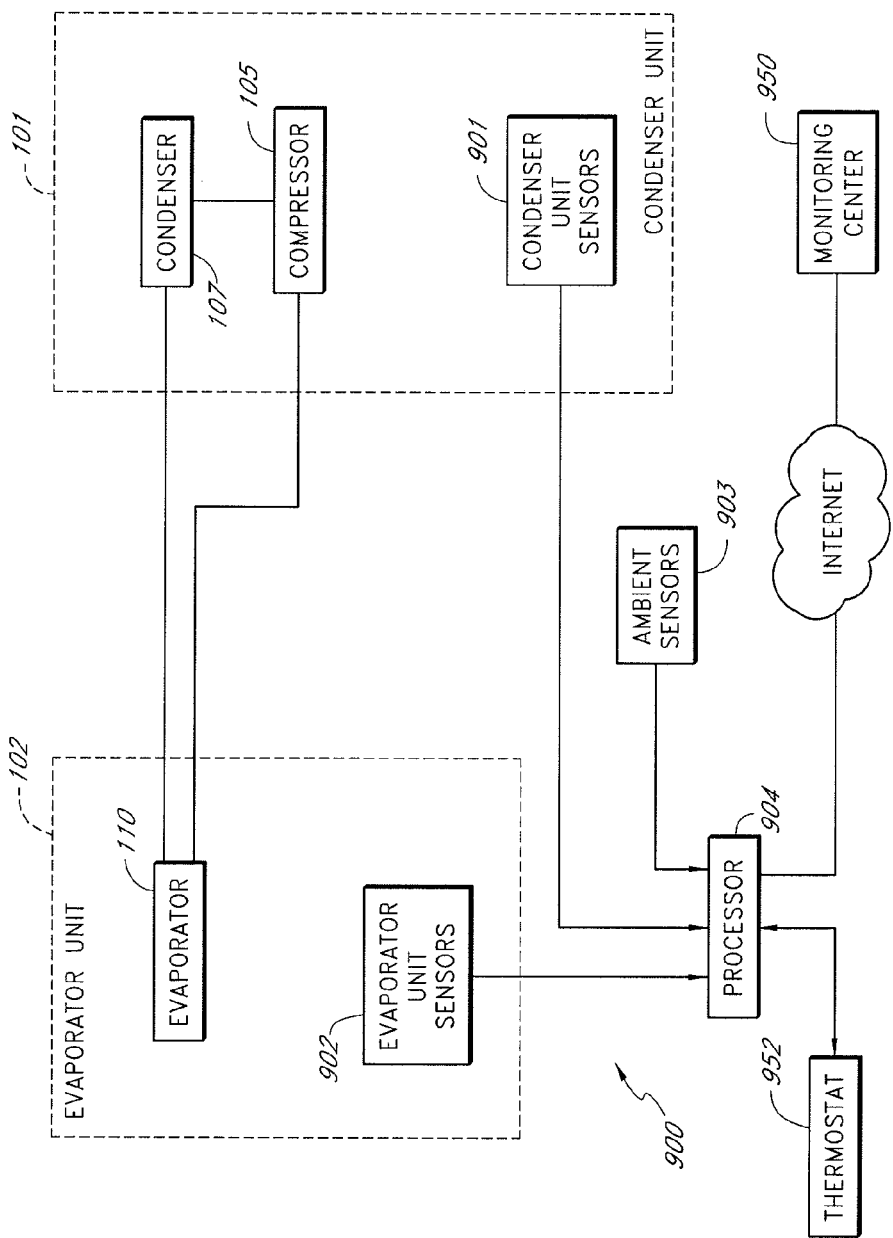

INTELLIGENT THERMOSTAT SYSTEM FOR LOAD MONITORING A REFRIGERANT-CYCLE APPARATUS

REFERENCE TO RELATED APPLICATION

This application is a divisional application of U.S. application Ser. No. 11/130,562, filed May 17, 2005, titled "INTELLIGENT THERMOSTAT SYSTEM FOR MONITORING A REFRIGERANT-CYCLE APPARATUS, which is a continuation application of U.S. application Ser. No. 10/916,222, filed Aug. 11, 2004, titled "METHOD AND APPARATUS FOR MONITORING REFRIGERANT-CYCLE SYSTEMS," the entire contents of which are hereby incorporated by reference.

BACKGROUND

1. Field of the Invention

The invention relates to monitoring system for measuring the operating and efficiency of a refrigerant-cycle system, such as, for example, an air conditioning system or refrigeration system.

2. Description of the Related Art

One of the major recurring expenses in operating a home or commercial building is the cost of providing electricity to the Heating Ventilating Air Conditioning (HVAC) system. If the HVAC system is not operating at peak efficiency, then the cost of operating the system increases unnecessarily. Each pound of refrigerant circulating in the system must do its share of the work. It must absorb an amount of heat in the evaporator or cooling coil, and it must dissipate this heat-plus some that is added in the compressor-through the condenser, whether air cooled, water cooled, or evaporative cooled. The work done by each pound of the refrigerant as it goes through the evaporator is reflected by the amount of heat it picks up from the refrigeration load, chiefly when the refrigerant undergoes a change of state from a liquid to a vapor.

For a liquid to be able to change to a vapor, heat must be added to or absorbed in it. This is what happens in the cooling coil. The refrigerant enters the metering device as a liquid and passes through the device into the evaporator, where it absorbs heat as it evaporates into a vapor. As a vapor, it makes its way through the suction tube or pipe to the compressor. Here it is compressed from a low temperature, low pressure vapor to a high temperature, high pressure vapor; then it passes through the high pressure or discharge pipe to the condenser, where it undergoes another change of state—from a vapor to a liquid—in which state it flows out into the liquid pipe and again makes its way to the metering device for another trip through the evaporator.

When the refrigerant, as a liquid, leaves the condenser it may go to a receiver until it is needed in the evaporator; or it may go directly into the liquid line to the metering device and then into the evaporator coil. The liquid entering the metering device just ahead of the evaporator coil will have a certain heat content (enthalpy), which is dependent on its temperature when it enters the coil, as shown in the refrigerant tables in the Appendix. The vapor leaving the evaporator will also have a given heat content (enthalpy) according to its temperature, as shown in the refrigerant tables.

The difference between these two amounts of heat content is the amount of work being done by each pound of refrigerant as it passes through the evaporator and picks up heat. The amount of heat absorbed by each pound of refrigerant is known as the refrigerating effect of the system, or of the refrigerant within the system.

Situations that can reduce the overall efficiency of the system include, refrigerant overcharge, refrigerant undercharge, restrictions in refrigerant lines, faulty compressor, excessive load, insufficient load, undersized or dirty duct work, clogged air filters, etc.

Unfortunately, modern HVAC systems do not include monitoring systems to monitor the operating of the system. A modern HVAC system is typically installed, charged with refrigerant by a service technician, and then operated for months or years without further maintenance. As long as the system is putting out cold air, the building owner or home owner assume the system is working properly. This assumption can be expensive; as the owner has no knowledge of how well the system is functioning. If the efficiency of the system deteriorates, the system may still be able to produce the desired amount of cold air, but it will have to work harder, and consume more energy, to do so. In many cases, the system owner does not have the HVAC system inspected or serviced until the efficiency has dropped so low that it can no longer cool the building. This is due in part, because servicing of an HVAC system requires specialized tools and knowledge that the typical building owner or home owner does not posses. Thus, the building owner or home owner, must pay for an expensive service call in order to have the system evaluated. Even if the owner does pay for a service call, many HVAC service technicians do not measure system efficiency. Typically, the HVAC service technicians are trained only to make rudimentary checks of the system (e.g., refrigerant charge, output temperature), but such rudimentary checks may not uncover other factors that can cause poor system efficiency. Thus, the typical building owner, or home owner, operates the HVAC system year after year not knowing that the system may be wasting money by operating at less than peak efficiency. Moreover, inefficiency use of electrical power can lead to brownouts and blackouts during heat waves or other periods of high air conditioning usage due to overloading of the electric power system (commonly referred to as the electric power grid).

SUMMARY

These and other problems are solved by a real-time monitoring system that monitors various aspects of the operation of a refrigerant system, such as, for example, an HVAC system, a refrigerator, a cooler, a freezer, a water chiller, etc. In one embodiment, the monitoring system is configured as a retrofit system that can be installed in an existing refrigerant system.

In one embodiment, the system includes a processor that measures power provided to the HVAC system and that gathers data from one or more sensors and uses the sensor data to calculate a figure of merit related to the efficiency of the system. In one embodiment, the sensors include one or more of the following sensors: a suction line temperature sensor, a suction line pressure sensor, a suction line flow sensor, a hot gas line temperature sensor, a hot gas line pressure sensor, a hot gas line flow sensor, a liquid line temperature sensor, a liquid line pressure sensor, a liquid line flow sensor. In one embodiment, the sensors include one or more of an evaporator air temperature input sensor, an evaporator air temperature output sensor, an evaporator air flow sensor, an evaporator air humidity sensor, and a differential pressure sensor. In one embodiment, the sensors include one or more of a condenser air temperature input sensor, a condenser air temperature output sensor, and a condenser air flow sensor, an evaporator air humidity sensor. In one embodiment, the sensors include one or more of an ambient air sensor and an ambient humidity sensor.

BRIEF DESCRIPTION OF THE DRAWINGS

FIG. 1 is a diagram of a typical refrigerant cycle system used in HVAC systems, refrigerators, freezers, and the like.

FIG. 9C is a block diagram of a monitoring system for monitoring the operation of the refrigerant-cycle system, where operating data for the system is provided to a monitoring service, such as, for example, a power company or monitoring canter, by using data transmission over a computer network.

DETAILED DESCRIPTION

Figure 1:
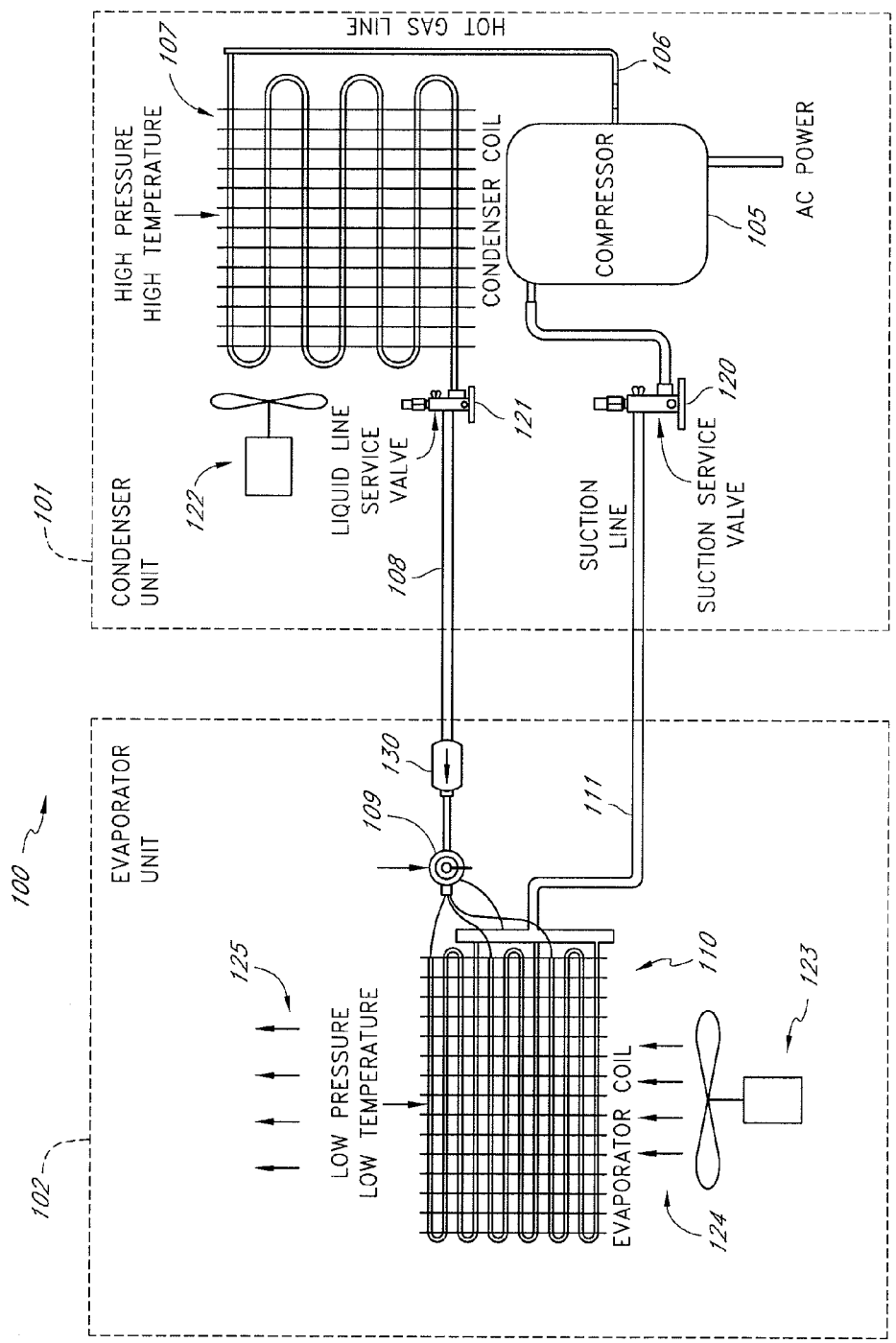

FIG. 1 is a diagram of a typical refrigerant cycle system 100 used in HVAC systems, refrigerators, freezers, and the like. In the system 100, a compressor provides hot compressed refrigerant gas to a hot gas line 106. The hot gas line provides the hot gas to a condenser 107. The condenser 107 cools the gas and condenses the gas into a liquid that is provided to a liquid line 108. The liquid refrigerant in the liquid line 108 is provided through a metering device 109 to an evaporator 110. The refrigerant expands back into a gas in the evaporator 110 and is provided back to the compressor though a suction line 110. A suction service valve 120 provides access to the suction line 111. A liquid line service valve 121 provides access to the liquid line 121. A fan 123 provides input air 124 to the evaporator 110. The evaporator cools the air and provides cooled evaporator output air 125. An optional drier/accumulator 130 can be provided in the liquid line 108. A fan 122 provides cooling air to the condenser 107.

The metering device 109 can be any refrigerant metering device as used in the art, such as, for example, a capillary tube, a fixed orifice, a Thermostatic eXpansion Valve (TXV), an electronically controlled valve, a pulsating solenoid valve, a stepper-motor valve, a low side float, a high-side float, an automatic expansion valve, etc. A fixed metering device such as a capillary tube or fixed orifice will allow some adjustment in system capacity as the load changes. As the outdoor condensing temperature increases, more refrigerant is fed through the metering device into the evaporator, increasing its capacity slightly. Conversely, as the heat load goes down, the outdoor condensing temperature goes down and less refrigerant is fed into the evaporator. For a location where the load does not vary widely, fixed metering devices my float with the load well enough. However, for climates where there is a relatively greater range in temperature variation, an adjustable metering device is typically used.

The system 100 cools the air through the evaporator 110 by using the refrigerating effect of an expanding gas. This refrigerating effect is rated in Btu per pound of refrigerant (Btu/lb); if the total heat load is known (given in Btu/hr), one can find the total number of pounds of refrigerant that must be circulated each hour of operation of the system. This figure can be broken down further to the amount that must be circulated each minute, by dividing the amount circulated per hour by 60.

Because of a small orifice in the metering device 109, when the compressed refrigerant passes from the smaller opening in the metering device to the larger tubing in the evaporator, a change in pressure occurs together with a change in temperature. This change in temperature occurs because of the vaporization of a small portion of the refrigerant (about 20%) and, in the process of this vaporization, the heat that is involved is taken from the remainder of the refrigerant.

Figure 2:
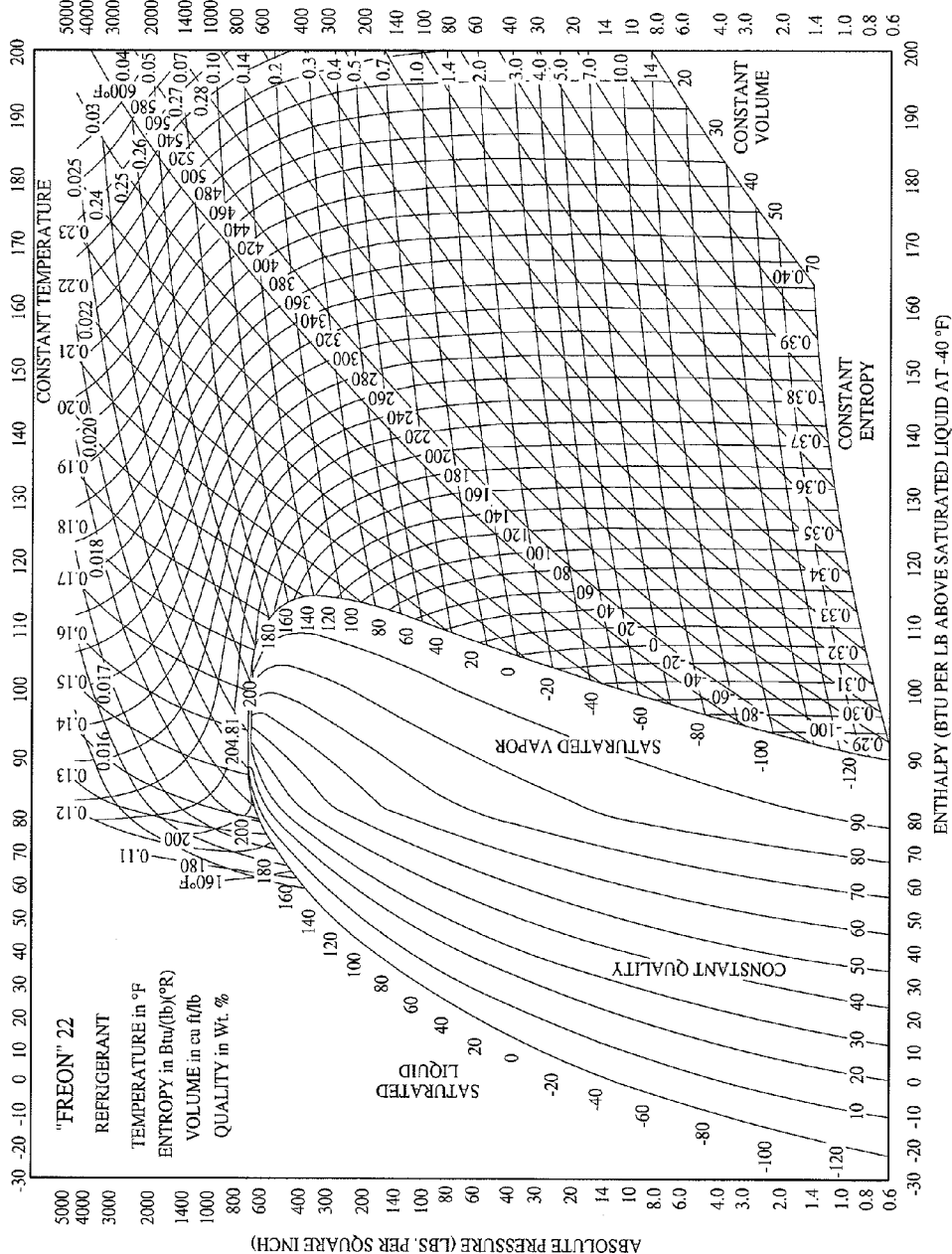
FIG. 2 is a detailed pressure-heat diagram of a typical refrigerant (R-22).

For example, from the table of saturated R-22 in FIG. 2, it can be seen that the heat content of 100° F. liquid is 39.27 BTU/lb and that of 40° F. liquid is 21.42 BTU/lb; this indicates that 17.85 BTU/lb has to be removed from each pound of refrigerant entering the evaporator. The latent heat of vaporization of 40° F. (17.85 BTU/lb) is 68.87 BTU/lb. This is another method of calculating the refrigerating effect, or work being done, by each pound of refrigerant under the conditions given.

The capacity of the compressor 105 should be such that it will remove from the evaporator that amount of refrigerant which has vaporized in the evaporator and in the metering device in order to get the necessary work done. The compressor 105 must be able to remove and send on to the condenser 107 the same weight of refrigerant vapor, so that it can be condensed back into a liquid and so continue in the refrigeration circuit 100 to perform additional work.

If the compressor 105 is unable to move this weight, some of the vapor will remain in the evaporator 110. This, in turn, will cause an increase in pressure inside the evaporator 110, accompanied by an increase in temperature and a decrease in the work being done by the refrigerant, and design conditions within the refrigerated space cannot be maintained.

A compressor 105 that is too large will withdraw the refrigerant from the evaporator 110 too rapidly, causing a lowering of the temperature inside the evaporator 110, so that design conditions will not be maintained.

In order for design conditions to be maintained within a refrigeration circuit, a balance between the requirements of the evaporator 110 and the capacity of the compressor 105 is maintained. This capacity is dependent on its displacement and on its volumetric efficiency. Volumetric efficiency depends on the absolute suction and discharge pressures under which the compressor 105 is operating.

In one embodiment, the system 1000 controls the speed of the compressor 105 to increase efficiency. In one embodiment, the system 1000 controls the metering device 109 to increase efficiency. In one embodiment, the system 1000 controls the speed of the fan 123 to increase efficiency. In one embodiment, the system 1000 controls the speed of the fan 122 to increase efficiency.

In the system 100, the refrigerant passes from the liquid stage into the vapor stage as it absorbs heat in the evaporator 110 coil. In the compressor 105 ion stage, the refrigerant vapor is increased in temperature and pressure, then the refrigerant gives off its heat in the condenser 107 to the ambient cooling medium, and the refrigerant vapor condenses back to its liquid state where it is ready for use again in the cycle.

Figure 3:
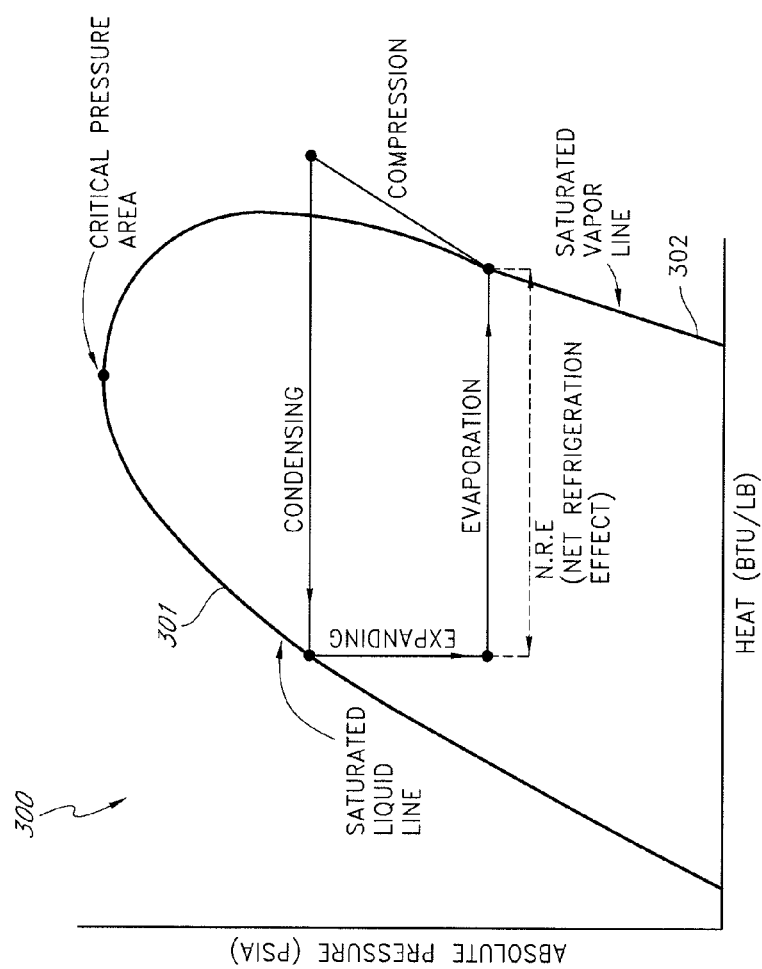
FIG. 3 is a pressure-heat diagram showing pressure-enthalpy changes through a refrigeration cycle.

FIG. 2 shows the pressure, heat, and temperature characteristics of this refrigerant. Enthalpy is another word for heat content. Diagrams such as FIG. 2 are referred to as pressure-enthalpy diagrams. Detailed pressure-enthalpy diagrams can be used for the plotting of the cycle shown in FIG. 2, but a basic or skeleton chart as shown in FIG. 3 is useful as a preliminary illustration of the various phases of the refrigerant circuit. There are three basic areas on the chart denoting changes in state between the saturated liquid line 301 and saturated vapor line 302 in the center of the chart. The area to the left of the saturated liquid line 301 is the subcooled area, where the refrigerant liquid has been cooled below the boiling temperature corresponding to its pressure; whereas the area to the right of the saturated vapor line 302 is the area of superheat, where the refrigerant vapor has been heated beyond the vaporization temperature corresponding to its pressure.

The construction of the diagram 300, illustrates what happens to the refrigerant at the various stages within the refrigeration cycle. If the liquid vapor state and any two properties of a refrigerant are known and this point can be located on the chart, the other properties can be determined from the chart.

If the point is situated anywhere between the saturated liquid 310 and vapor lines 302, the refrigerant will be in the form of a mixture of liquid and vapor. If the location is closer to the saturated liquid line 301, the mixture will be more liquid than vapor, and a point located in the center of the area at a particular pressure would indicate a 50% liquid 50% vapor situation.

The change in state from a vapor to a liquid, the condensing process, occurs as the path of the cycle develops from right to left; whereas the change in state from a liquid to a vapor, the evaporating process, travels from left to right. Absolute pressure is indicated on the vertical axis at the left, and the horizontal axis indicates heat content, or enthalpy, in BTU/lb.

The distance between the two saturated lines 310, 302 at a given pressure, as indicated on the heat content line, amounts to the latent heat of vaporization of the refrigerant at the given absolute pressure. The distance between the two lines of saturation is not the same at all pressures, for they do not follow parallel curves. Therefore, there are variations in the latent heat of vaporization of the refrigerant, depending on the absolute pressure. There are also variations in pressure-enthalpy charts of different refrigerants and the variations depend on the various properties of the individual refrigerants.

There is relatively little temperature change of the condensed refrigeration liquid after it leaves the condenser 107 and travels through the liquid line 108 on its way to the expansion or metering device 109, or in the temperature of the refrigerant vapor after it leaves the evaporator 110 and passes through the suction line 111 to the compressor 105.

Figure 4:
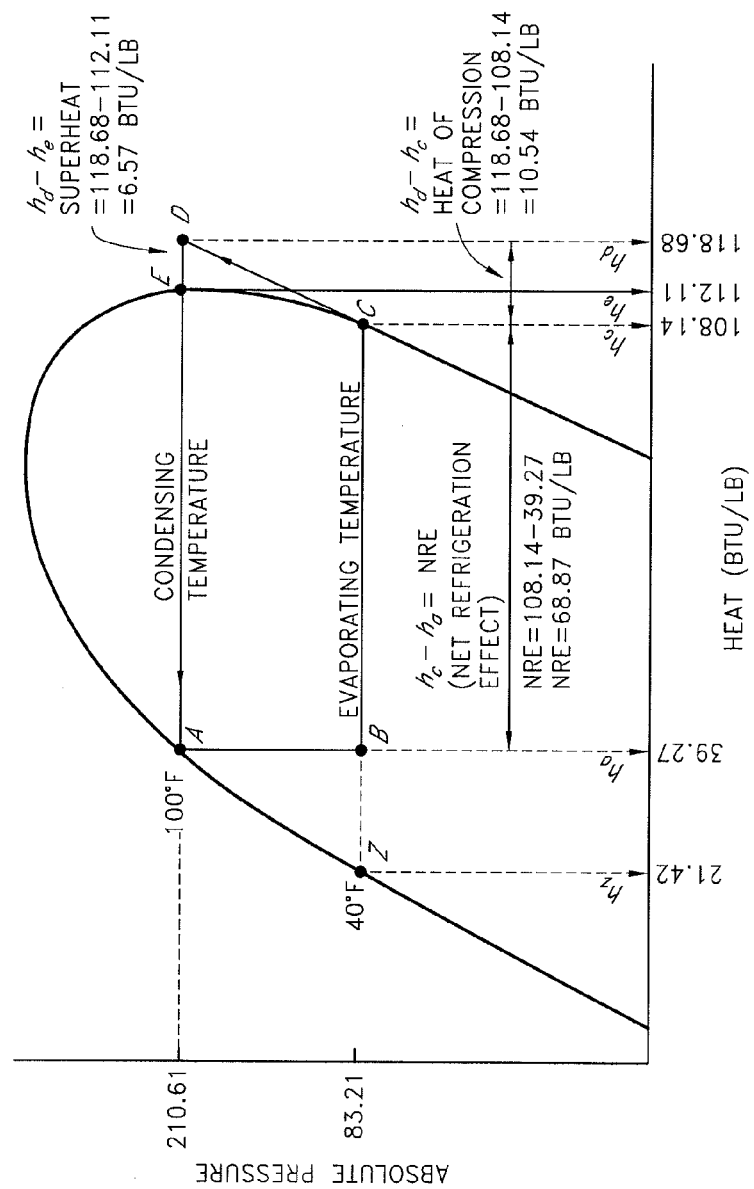
FIG. 4 is a pressure-heat diagram showing pressure, heat, and temperature values for a refrigeration cycle operating with a 40° F. evaporator.

FIG. 4 shows the phases of the simple saturated cycle with appropriate labeling of pressures, temperatures, and heat content or enthalpy. Starting at point A on the saturated liquid where all of the refrigerant vapor at 100° F. has condensed into liquid at 100° F. and is at the inlet to the metering device, between points A and B is the expansion process as the refrigerant passes through the metering device 109; and the refrigerant temperature is lowered from the condensation temperature of 100° F. to the evaporating temperature of 40° F.

When the vertical line A-B (the expansion process) is extended downward to the bottom axis, a reading of 39.27 BTU/lb is indicated, which is the heat content of 100° F. liquid. To the left of point B at the saturated liquid line 108 is point Z, which is also at the 40° F. temperature line. Taking a vertical path downward from point Z to the heat content line, a reading of 21.42 BTU/lb is indicated, which is the heat content of 40° F. liquid.

The horizontal line between points B and C indicates the vaporization process in the evaporator 110, where the 40° F. liquid absorbs enough heat to completely vaporize the refrigerant. Point C is at the saturated vapor line, indicating that the refrigerant has completely vaporized and is ready for the compression process. A line drawn vertically downward to where it joins the enthalpy line indicates that the heat content, shown at $h_c$ is 108.14 Btu/lb, and the difference between $h_a$ and $h_c$ is 68.87 Btu/lb, which is the refrigerating effect, as shown in an earlier example.

The difference between points $h_e$ and $h_c$ on the enthalpy line amounts to 86.72 Btu/lb, which is the latent heat of vaporization of 1 lb of R-22 at 40° F. This amount would also exhibit the refrigerating effect, but some of the refrigerant at 100° F. must evaporate or vaporize in order that the remaining portion of each pound of R-22 can be lowered in temperature from 100° F. to 40° F.

All refrigerants exhibit properties of volume, temperature, pressure, enthalpy or heat content, and entropy when in a gaseous state. Entropy is defined as the degree of disorder of the molecules that make up. In refrigeration, entropy is the ratio of the heat content of the gas to its absolute temperature in degrees Rankin.

The pressure-enthalpy chart plots the line of constant entropy, which stays the same provided that the gas is compressed and no outside heat is added or taken away. When the entropy is constant, the compression process is called adiabatic, which means that the gas changes its condition without the absorption or rejection of heat either from or to an external body or source. It is common practice, in the study of cycles of refrigeration, to plot the compression line either along or parallel to a line of constant entropy.

Figure 5:
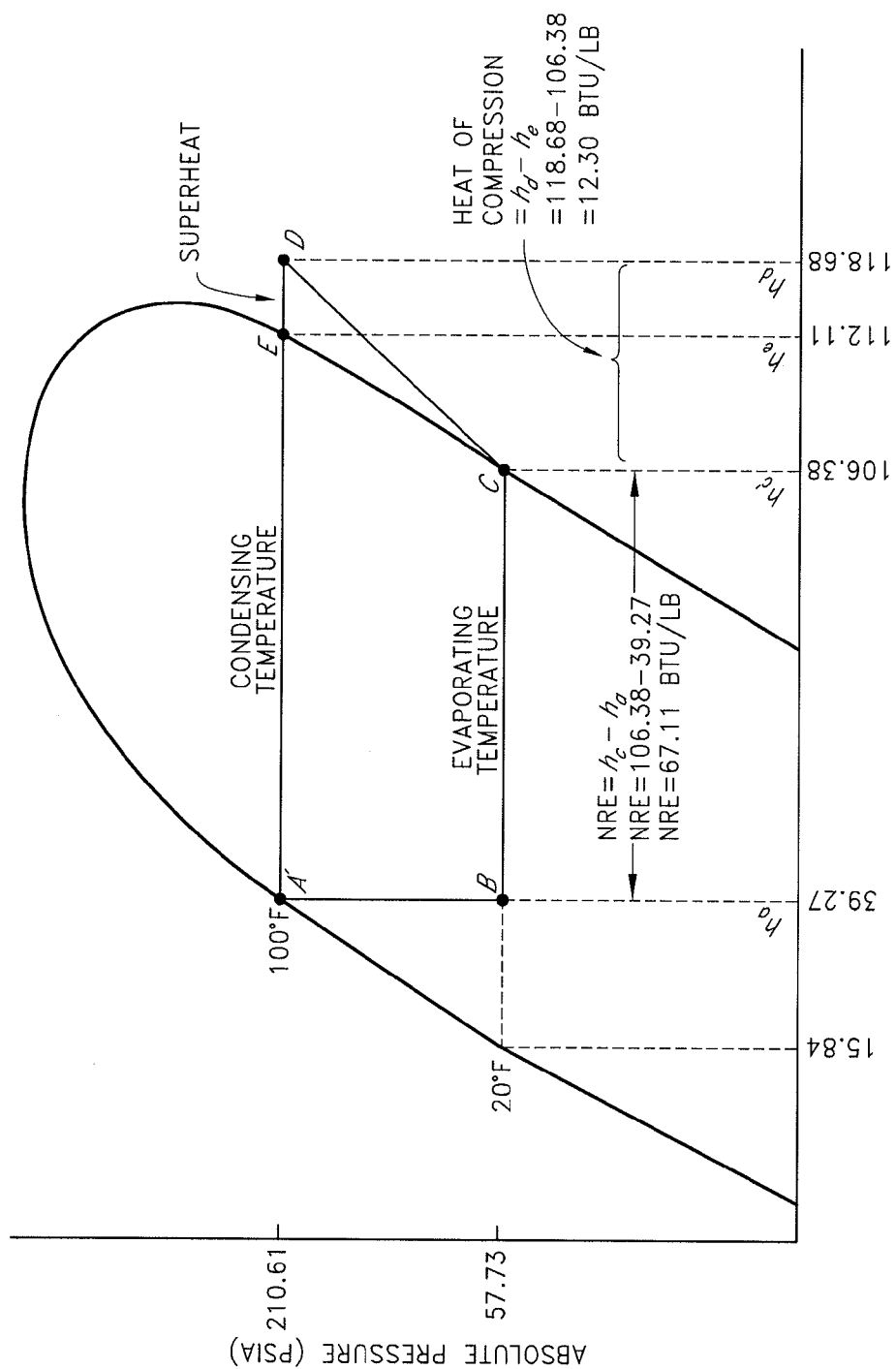
FIG. 5 is a pressure-heat diagram showing pressure, heat, and temperature values for a refrigeration cycle operating with a 20° F. evaporator.

In FIG. 5, line C-D denotes the compression process, in which the pressure and temperature of the vapor are increased from that in the evaporator 110 to that in the condenser 107, with the assumption that there has been no pickup of heat in the suction line 111 between the evaporator 110 and the compressor 105. For a condensing temperature of 100° F., a pressure gauge would read approximately 196 psig; but the chart is rated in absolute pressure and the atmospheric pressure of 14.7 are added to the psig, making it actually 210.61 psia.

Point D on the absolute pressure line is equivalent to the 100° F. condensing temperature; it is not on the saturated vapor line, it is to the right in the superheat area, at a junction of the 210.61 psia line, the line of constant entropy of 40° F., and the temperature line of approximately 128° F. A line drawn vertically downward from point D intersects the heat content line at 118.68 Btu/lb, which is $h_d$, the difference between $h_c$ and hd, is 10.54 Btu/lb—the heat of compression that has been added to the vapor. This amount of heat is the heat energy equivalent of the work done during the refrigeration compression cycle. This is the theoretical discharge temperature, assuming that saturated vapor enters the cycle; in actual operation, the discharge temperature may be 20° to 35° higher than that predicted theoretically. This can be checked in the system 100 by attaching a temperature sensor 1016 to the hot gas line 106.

During the compression process, the vapor is heated by the action of its molecules being pushed or compressed closer together, commonly called heat of compression.

Line D-E denotes the amount of superheat that must be removed from the vapor before it can commence the condensation process. A line drawn vertically downward from point E to point $h_e$ on the heat content line indicates the distance $h_d$-$h_e$, or heat amounting to 6.54 Btu/lb, since the heat content of 100° F. vapor is 112.11 Btu/lb. This superheat is usually removed in the hot gas discharge line or in the upper portion of the condenser 107. During this process the temperature of the vapor is lowered to the condensing temperature.

Line E-A represents the condensation process that takes place in the condenser 107. At point E the refrigerant is a saturated vapor at the condensing temperature of 100° F. and an absolute pressure of 210.61 psia; the same temperature and pressure prevail at point A, but the refrigerant is now in a liquid state. At any other point on line E-A the refrigerant is in the phase of a liquid vapor combination; the closer the point is to A, the greater the amount of the refrigerant that has condensed into its liquid stage. At point A, each pound of refrigerant is ready to go through the refrigerant cycle again as it is needed for heat removal from the load in the evaporator 110.

Two factors that determine the coefficient of performance (COP) of a refrigerant are refrigerating effect and heat of compression. The equation may be written as $$COP = \frac{refrigerating\_effect}{heat\_of\_compression} \qquad (1)$$

Substituting values, from the pressure-enthalpy diagram of the simple saturated cycle previously presented, the equation would be:

$$COP = \frac{h_c - h_a}{h_d - h_c} = \frac{68.87}{10.54} = 6.53$$

The COP is, therefore, a rate or a measure of the theoretical efficiency of a refrigeration cycle is the energy that is absorbed in the evaporation process divided by the energy supplied to the gas during the compression process. As can be seen from Equation 1, the less energy expended in the compression process, the larger will be the COP of the refrigeration system.

The pressure-enthalpy diagrams in FIGS. 4 and 5 show a comparison of two simple saturated cycles having different evaporating temperatures, to bring out various differences in other aspects of the cycle. In order that an approximate mathematical calculation comparison may be made, the cycles shown in FIGS. 4 and 5 will have the same condensing temperature, but the evaporating temperature will be lowered 20° F. The values of A, B, C, D, and E from FIG. 4 as the cycle are compared to that in FIG. 5 (with a 20° F. evaporator 110). The refrigerating effect, heat of compression, and the heat dissipated at the condenser 107 in each of the refrigeration cycles will be compared. The comparison will be based on data about the heat content or enthalpy line, rated in Btu/lb.

For the 20° F. evaporating temperature cycle shown in FIG. 5:

Net refrigerating effect ($h_c$-$h_a$)=67.11 Btu/lb

Heat of compression ($h_d$-$h_c$)=67.11 Btu/lb

Comparing the data above with those of the cycle with the 40° F. evaporating temperature FIG. 4, shows that there is a decrease in the net refrigeration effect (NRE) of 2.6% and an increase in the heat of compression of 16.7%. There will be some increase in superheat, which should be removed either in the hot gas line 106 or the upper portion of the condenser 107. This is the result of a lowering in the suction temperature, the condensing temperature remaining the same.

From Equation 1, it follows that the weight of refrigerant to be circulated per ton of cooling, in a cycle with a 20° F. evaporating temperature and a 100° F. condensing temperature, is 2.98 lb/min/ton:

$$W = \frac{200\,(\text{Btu/min})}{NRE\,(\text{Btu/lb})}$$

$$= \frac{200\,\text{Btu/min}}{67.11\,\text{Btu/lb}}$$

$$= 2.98\,\text{lb/min}$$

Circulating more refrigerant typically involves either a larger compressor 105, or the same size of compressor 105 operating at a higher rpm.

Figure 6:
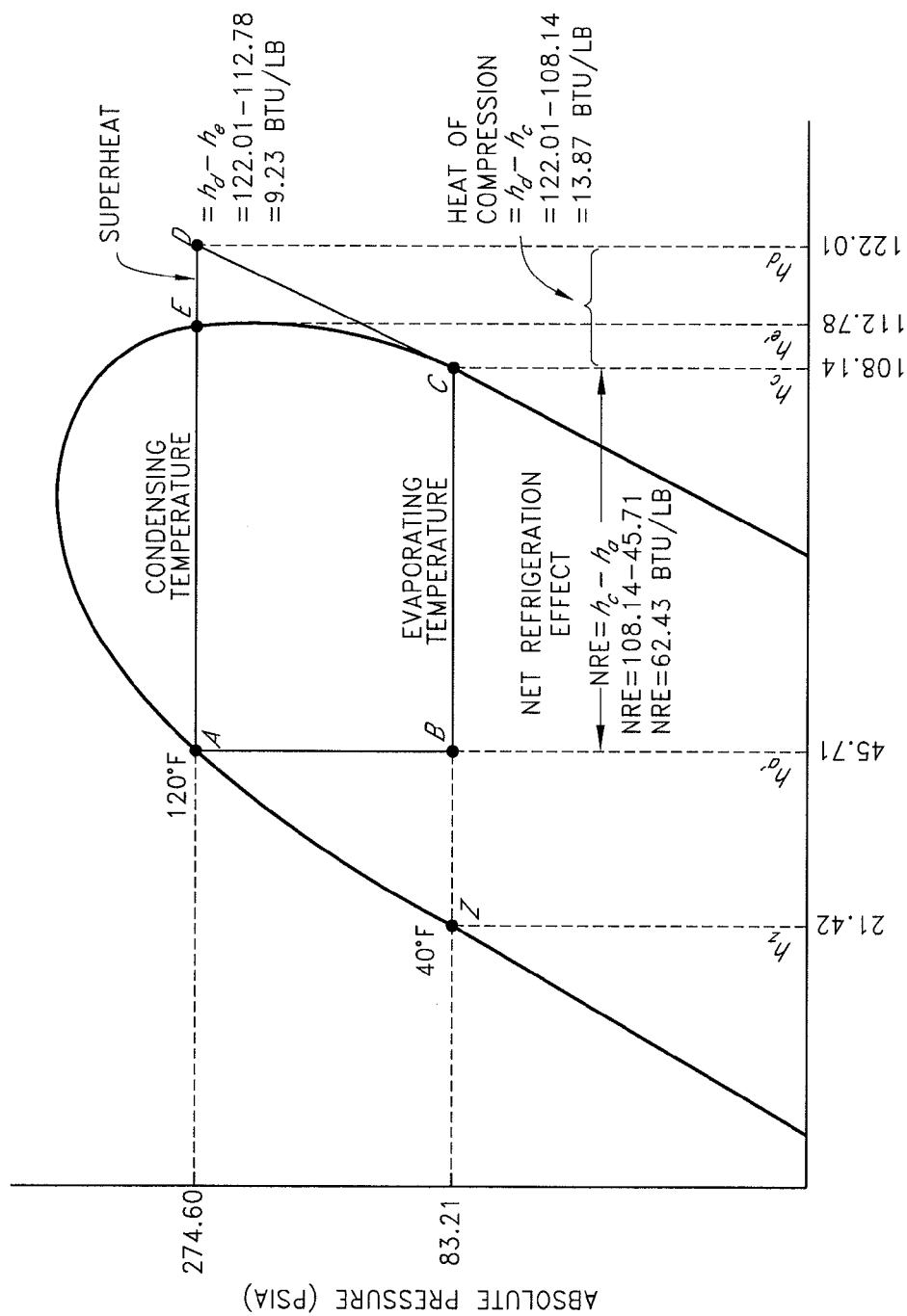
FIG. 6 is a pressure-heat diagram showing the cycle of FIG. 4 with a 40° F. evaporating temperature, where the condensing temperature has been increased to 120° F.

FIG. 6 shows the original cycle with a 40° F. evaporating temperature, but the condensing temperature has been increased to 120° F.

Figure 7:
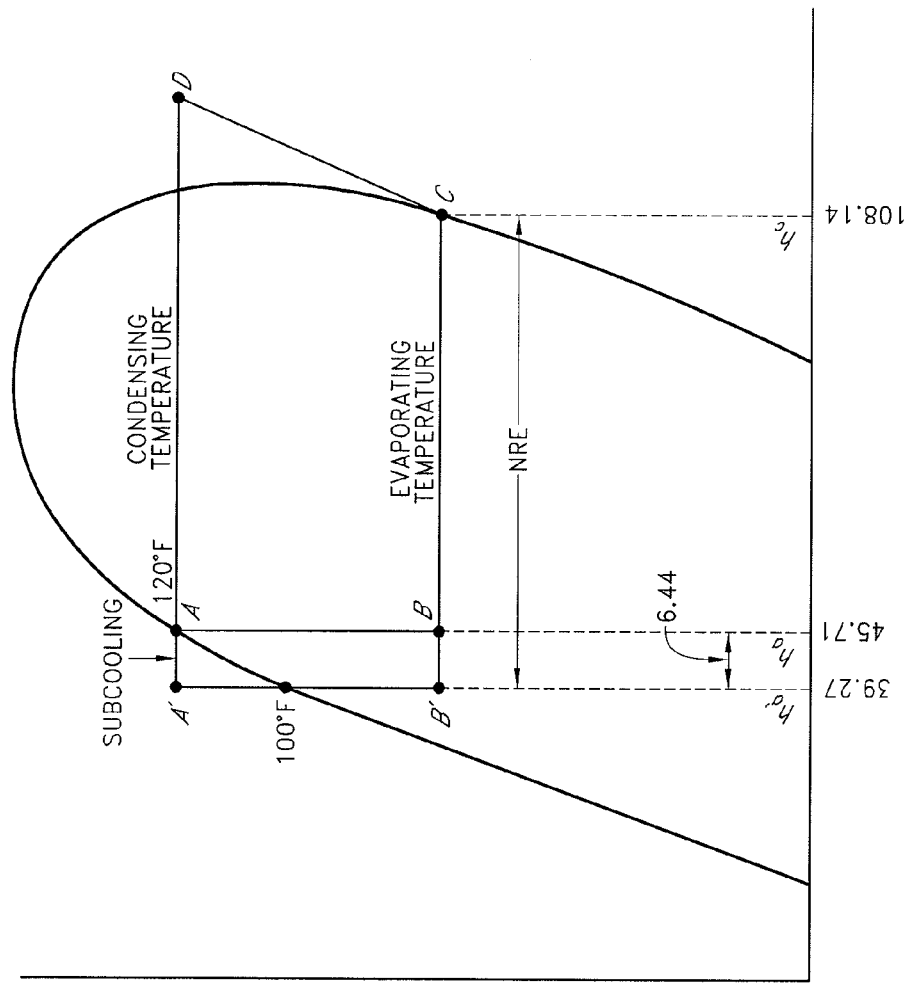
FIG. 7 is a pressure-heat diagram showing how subcooling by the condenser improves the refrigeration effect and the COP.

Again taking the specific data from the heat content or enthalpy line, one now finds for the 120° F. condensing temperature cycle that $h_a=45.71$, $h_c=108.14$, $h_d=122.01$, and $h_e=112.78$. Thus, the net refrigerating effect $(h_c-h_a)=62.43$ Btu/lb, the heat of compression $(h_d-h_c)=13.87$ Btu/lb, and the condenser 107 superheat $(h_d-h_e)=9.23$ Btu/lb In comparison with the cycle having the 100° F. condensing temperature (FIG. 4), the cycle can also be calculated by allowing the temperature of the condensing process to increase to 120° F. (as shown in FIG. 7). FIG. 7 shows a decrease in the NRE of 9.4%, an increase in heat of compression of 31.6%, and an increase of superheat to be removed either in the discharge line or in the upper portion of the condenser 107 of 40.5%.

With a 40° F. evaporating temperature and a 120° F. condensing temperature, the weight of refrigerant to be circulated will be 3.2 lb/min/ton. This indicates that approximately 10% more refrigerant must be circulated to do the same amount of work as when the condensing temperature was 100° F.

Both of these examples show that for the beset efficiency of a system, the suction temperature should be as high as feasible, and the condensing temperature should be as low as feasible. Of course, there are limitations as to the extremes under which the system 100 may operate satisfactorily, and other means of increasing efficiency must then be considered. Economics of equipment (cost+operating performance) ultimately determine the feasibility range.

Figure 8:
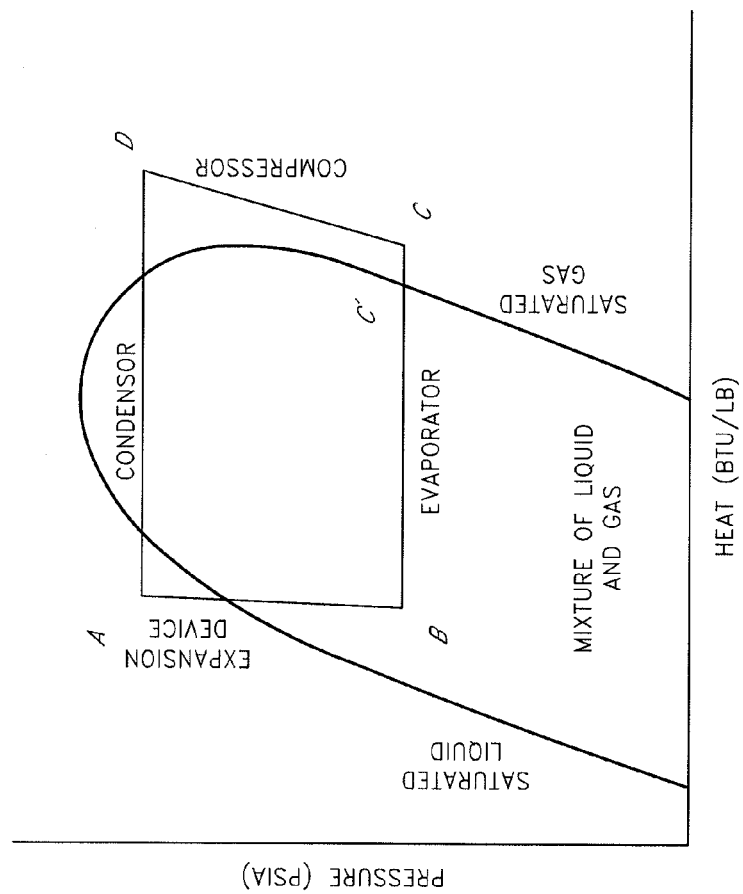
FIG. 8 is a pressure-heat diagram showing the cooling process in the evaporator.

Referring to FIG. 8, after the condensing process has been completed and all of the refrigerant vapor at 120° F. is in the liquid state, if the liquid can be subcooled to point A' on the 100° F. line (a difference of 20° F.), the NRE $(h_c-h_a)$ will be increased 6.44 Btu/lb. This increase in the amount of heat absorbed in the evaporator 110 without an increase in the heat of compression will increase the COP of the cycle, since there is no increase in the energy input to the compressor 105.

This subcooling can take place while the liquid is temporarily in storage in the condenser 107 or receiver, or some of the liquid's heat may be dissipated to the ambient temperature as it passes through the liquid pipe on its way to the metering device. Subcooling can also take place in a commercial type water cooled system through the use of a liquid subcooler.

Normally, the suction vapor does not arrive at the compressor 105 in a saturated condition. Superheat is added to the vapor after the evaporating process has been completed, in the evaporator 110 and/or in the suction line 111, as well as in the compressor 105. If this superheat is added only in the evaporator 110, it is doing some useful cooling; for it too is removing heat from the load or product, in addition to the heat that was removed during the evaporating process. But if the vapor is superheated in the suction line 111 located outside of the conditioned space, no useful cooling is accomplished; yet this is what takes place in many system.

In the system 100, the refrigerant pressure is relatively high in the condenser 107 and relatively low in the evaporator 110. A pressure rise occurs across the compressor 105 and a pressure drop occurs across the metering device 109. Thus, the compressor 105 and the metering device maintain the pressure difference between the condenser 107 and the evaporator 110.

Thus, a refrigeration system can be divided into the high side and low side portions. The high side contains the high pressure vapor and liquid refrigerant and is the part of the system that rejects heat. The low side contains the low pressure liquid vapor and refrigerant and is the side that absorbs heat.

Heat is always trying to reach a state of balance by flowing from a warmer object to a cooler object. Heat only flows in one direction, from warmer to cooler. Temperature difference (TD) is what allows heat to flow from one object to another. The greater the temperature difference the more rapid the heat flow. For the high side of a refrigeration unit to reject heat its temperature must be above the ambient or surrounding temperature. For the evaporator 110 to absorb heat, its temperature must be below the surrounding ambient temperature.

Two factors that affect the quantity of heat transferred between two objects are the temperature difference and the mass of the two objects. The greater the temperature difference between the refrigerant coil (e.g., the condenser 107 or the evaporator 110) and the surrounding air, the more rapid will be the heat transfer. The larger the size of the refrigerant coil, the greater the mass of refrigerant, which also increases the rate of heat transfer. Engineers can either design coils to have high temperature differences or larger areas to increase the heat transfer rate.

To increase energy efficiency, systems are designed with larger coils because it is more efficient to have a lower temperature and a larger area to transfer heat. It takes less energy to produce a smaller pressure/temperature difference within a refrigeration system. Manufacturers of new high efficiency air conditioning systems use this principle.

The same principle can be applied to the evaporator 110 coils. The temperature differences between the evaporator input air 124 and the evaporator output air 125 are lower than they were on earlier systems. Older, lower efficiency, air conditioning systems may have evaporative coils that operate at 35° F. output temperature, while newer higher efficiency evaporator 110 may operate in the 45° F. output range. Both evaporators 110 can pick up the same amount of heat provided that the higher temperature, higher efficiency coil has greater area and, therefore, more mass of refrigerant being exposed to the air stream to absorb heat. The higher evaporative coil temperature may produce less dehumidification. In humid climates, de-humidification can be an important part of the total air conditioning.

Correct equipment selection is important to ensure system operation and to obtain desired energy efficiencies. Previously, it was a common practice in many locations for installers to select an evaporator 110 of a different tonnage than the condenser unit 101 capacity. While this practice in the past may provide higher efficiencies, for most of today's more technically designed systems proper matching is usually achieved by using the manufacturer's specifications in order to provide proper operation. Mismatching systems can result in poor humidity control and higher operating costs. In addition to poor energy efficiency and lack of proper humidity control, the compressor 105 in a mismatched system may not receive adequate cooling from returning refrigerant vapor. As a result the compressor 105 temperature will be higher, and this can reduce the life of the compressor 105.

As refrigerant vapor leaves the discharge side of a compressor 105, it enters the condenser 107. As this vapor travels through the condenser 107, heat from the refrigerant dissipates to the surrounding air through the piping and fins. As heat is removed, the refrigerant begins to change state from vapor to liquid. As the mixture of liquid and vapor continues to flow through the condenser 107, more heat is removed and eventually all, or virtually all, of the vapor has transformed into liquid. The liquid flows from the outlet of the condenser 107 through the liquid line 108 to the metering device 109.

The high pressure, high temperature liquid refrigerant passes through the metering device 109 where its temperature and pressure change. As the pressure and temperature change, some of the liquid refrigerant boils off forming flash gas. As this mixture of refrigerant, liquid, and vapor flow through the evaporator 110, heat is absorbed, and the remaining liquid refrigerant changes into a vapor. At the outlet of the evaporator 110 the vapor flows back through the suction line 111 to the compressor 105.

The compressor 105 draws in this low pressure, low temperature vapor and converts it to a high temperature, high pressure vapor where the cycle begins again.

An ideally sized and functioning system 100 is one where the last bit of refrigerant vapor changes into a liquid at the end of the condenser 107 and where the last bit of liquid refrigerant changes into a vapor at the end of the evaporator 110. However, because it is impossible to have a system operate at this ideal state, units are designed to have some additional cooling, called subcooling, of the liquid refrigerant to ensure that no vapor leaves the condenser 107. Even a small amount of vapor leaving a condenser 107 can significantly reduce efficiency of the system 100.

On the evaporator 110 side a small amount of additional temperature is added to the refrigerant vapor, called superheat, to ensure that no liquid refrigerant returns to the compressor 105. Returning liquid refrigerant to the compressor 105 can damage the compressor 105.

Systems that must operate under a broad range of temperature conditions will have difficulty maintaining the desired level of subcooling and superheat. There are two components that can be used in these systems to enhance the level of efficiency and safety in operation. They are the receiver and the accumulator. The receiver is placed in the liquid line 108 and holds a little extra refrigerant so the system has enough for high loads on hot days. The accumulator is placed in the suction line 111 and traps any the liquid refrigerant that would flow back to the compressor 105 on cool days with light loads.

A liquid receiver can be located at the end of the condenser 107 outlet to collect liquid refrigerant. The liquid receiver allows the liquid to flow into the receiver and any vapor collected in the receiver to flow back into the condenser 107 to be converted back into a liquid. The line connecting the receiver to the condenser 107 is called the condensate line and must be large enough in diameter to allow liquid to flow into the receiver and vapor to flow back into the condenser 107. The condensate line must also have a slope toward the receiver to allow liquid refrigerant to freely flow from the condenser 107 into the receiver. The outlet side of the receiver is located at the bottom where the trapped liquid can flow out of the receiver into the liquid line.

Receivers should be sized so that all of the refrigerant charge can be stored in the receiver. Some refrigeration condensing units come with receivers built into the base of the condensing unit The accumulator is located at the end of the evaporator 110 and allows liquid refrigerant to be collected in the bottom of the accumulator and remain there as the vapor refrigerant is returned to the compressor 105. The inlet side of the accumulator is connected to the evaporator 110 where any liquid refrigerant and vapor flow in. The outlet of the accumulator draws vapor through a U shaped tube or chamber. There is usually a small port at the bottom of the U shaped tube or chamber that allows liquid refrigerant and oil to be drawn into the suction line. Without this small port, refrigerant oil would collect in the accumulator and not return to the compressor 105. The small port does allow some liquid refrigerant to enter the suction line. However, it is such a small amount of liquid refrigerant that it boils off rapidly, so there is little danger of liquid refrigerant flowing into the compressor 105.

Accumulators are often found on heat pumps. During the changeover cycle, liquid refrigerant can flow back out of the outdoor coil. This liquid refrigerant could cause compressor 105 damage if it were not for the accumulator, which blocks its return.

The pressure-heat diagram of FIG. 8 shows the cooling process in the evaporator 110. Initially the high pressure liquid is usually subcooled 8-10° F. or more. When subcooled liquid from point A flows through the expansion device 109, its pressure drops to the pressure of the evaporator 110. Approximately 20% of the liquid boils off to gas, cooling the remaining liquid-gas mixture. Its total heat (enthalpy) at point B is relatively unchanged from A. No external heat energy has been exchanged. From points B to C, the remainder of the liquid boils off, absorbing the heat flowing in from the evaporator 110 load (air, water, etc.). At point C, all of the liquid has evaporated and the refrigerant is vapor at the saturation temperature corresponding to the evaporator 110 pressure.

The subcooling increases cycle efficiency and can prevent flash gas due to pressure loss from components, pipe friction, or increase in height.

Many smaller refrigeration systems are designed to have the expansion device control the refrigerant flow so the evaporator 110 will heat the vapor beyond saturated conditions and ensure no liquid droplets will enter and possibly damage the compressor 105. It is assumed here for the sake of simplicity there is no pressure drop through the evaporator 110. In reality there are pressure drops which would slightly shift the evaporating and condensing processes from the constant pressure lines shown.

If the evaporator 110 does not have to superheat refrigerant vapor, it can produce more cooling capacity. On smaller systems the difference is relatively small and it is more important to protect the compressor 105. On larger systems, an increase in evaporator performance can be important. A flooded evaporator 10 absorbs heat from points B to C. It can circulate more pounds of refrigerant (more cooling capacity) per square foot of heat transfer surface.

An undersized evaporator with less heat transfer surface will not handle the same heat load at the same temperature difference as a correctly sized evaporator. The new balance point will be reached with a lower suction pressure and temperature. The load will be reduced and the discharge pressure and temperature will also be reduced. An undersized evaporator and a reduced hat load both have similar effect on the refrigerant cycle because they both are removing less heat from the refrigerant.

As the ambient temperature increase, the load on the evaporator increases. When the load on the evaporator increase, the pressures increase. The operating points shift up and to the right on the pressure-heat curve. As the load on the evaporator decreases, the load on the evaporator decreases, and the pressures decrease. The operating points on the pressure-heat curve shift down. Thus, knowledge of the ambient temperature is useful in determining whether the system 100 is operating efficiency.

Figure 9A:
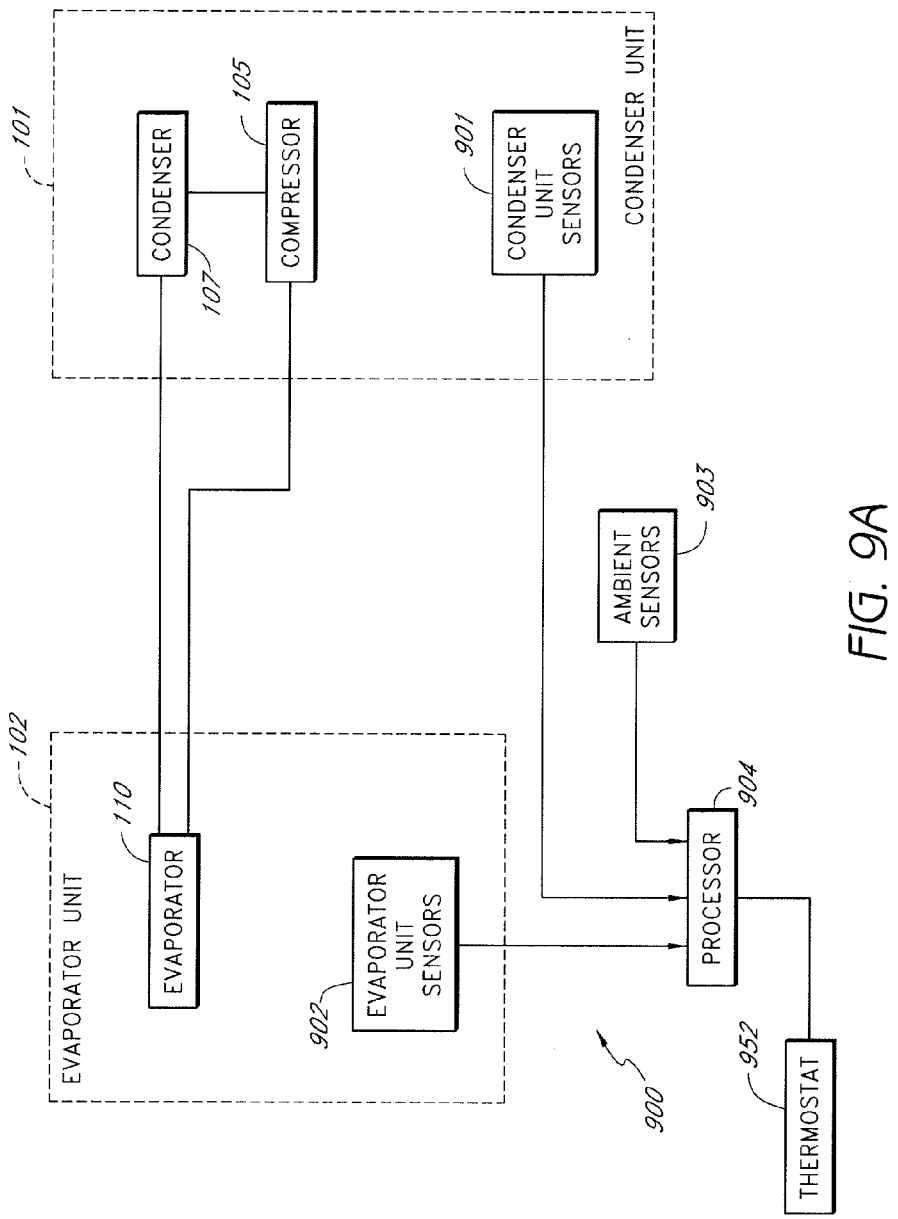
FIG. 9A is a block diagram of a monitoring system for monitoring the operation of the refrigerant-cycle system.

FIG. 9A is a block diagram of a monitoring system 900 for monitoring the operation of the refrigerant-cycle system. In FIG. 9A, one or more condenser unit sensors 901 measure operating characteristics of the elements of the condenser unit 101, one or more evaporator unit sensors 902 measure operating characteristics of the evaporator unit 102, and one or more ambient sensors 903 measure ambient conditions. Sensor data from the condenser unit sensors 901, evaporator unit sensors 902, and condenser unit sensors 903 are provided to a processing system 904. The processing system 904 uses the sensor data to calculate system efficiency, identify potential performance problems, calculate energy usage, etc. In one embodiment, the processing system 904 calculates energy usage and energy costs due to inefficient operation. In one embodiment, the processing system 904 schedules filter maintenance according to elapsed time and/or filter usage. In one embodiment, the processing system 904 identifies potential performance problems, (e.g., low airflow, Insufficient or unbalanced load, excessive load, low ambient temperature, high ambient temperature, refrigerant undercharge, refrigerant overcharge, liquid line restriction, suction line restriction, hot gas line restriction, inefficient compressor, etc.). In one embodiment, the processing system 904 provides plots or charts of energy usage and costs. In one embodiment, the processing system 904 the monitoring system provides plots or charts of the additional energy costs due to inefficient operation of the refrigerant-cycle system. In one embodiment, a thermostat 952 is provided to the processing system 904. In one embodiment, the processing system 904 and thermostat 952 are combined.

Figure 9B:
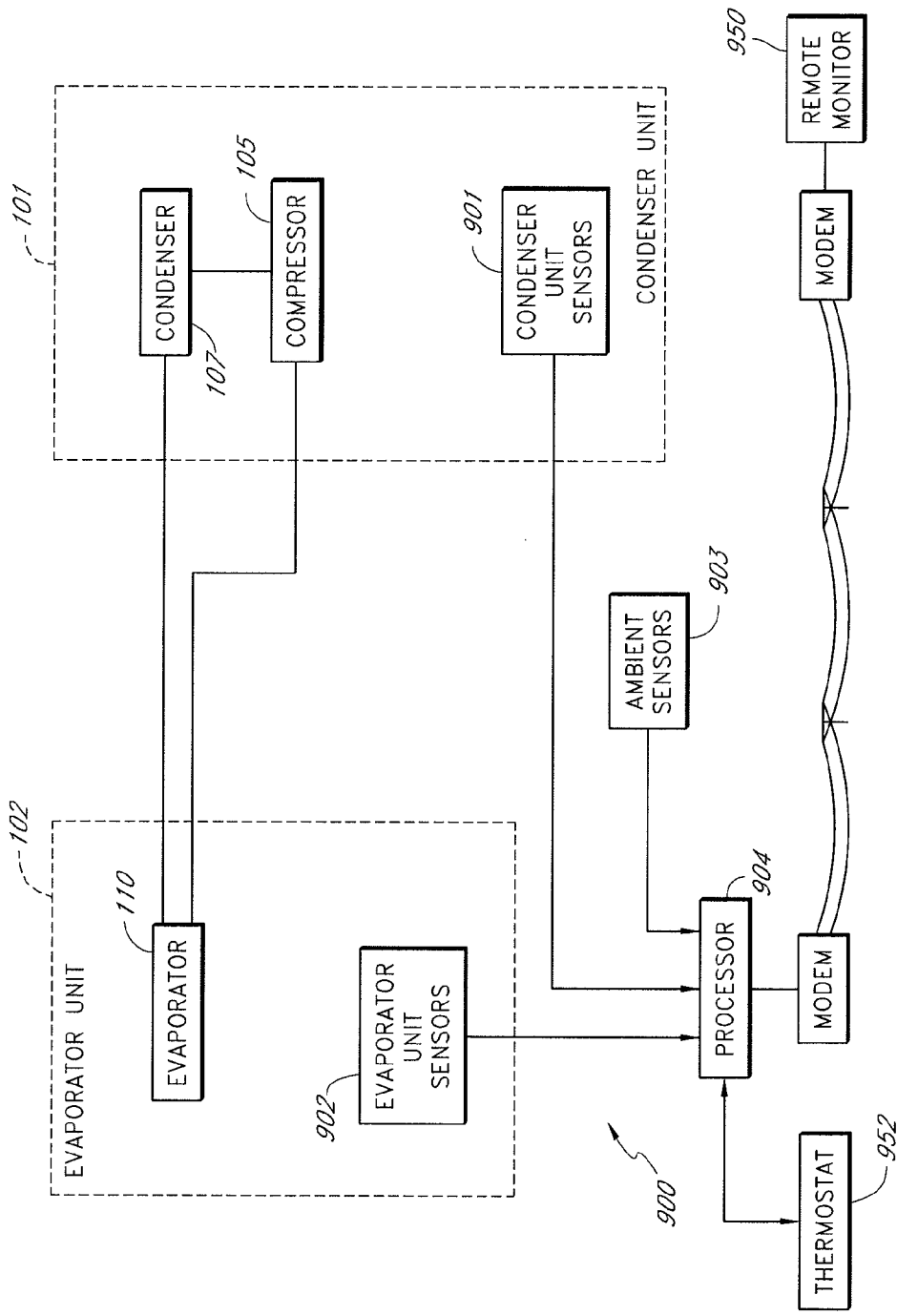
FIG. 9B is a block diagram of a monitoring system for monitoring the operation of the refrigerant-cycle system, where operating data for the system is provided to a monitoring service, such as, for example, a power company or monitoring center, by using data transmission over power lines.

FIG. 9B is a block diagram of the system 900 wherein operating data from the refrigerant-cycle system is provided to a remote monitoring service 950, such as, for example, a power company or monitoring center. In one embodiment, the system 900 provides operating data related to the operating efficiency of the refrigerant-cycle system to the remote monitor 950. In one embodiment, the remote monitoring service provides operating efficiency data to an electric power company or governmental agency.

Data can be transmitted from the system 900 to a remote monitoring service by using data transmission over power lines as shown in FIG. 9B and/or by using data transmission over a data network (e.g., the Internet, a wireless network, a cable modem network, a telephone network, etc.) as shown in FIG. 9B and also as shown in discussed in connection with FIGS. 9F-H.

Figure 9D:
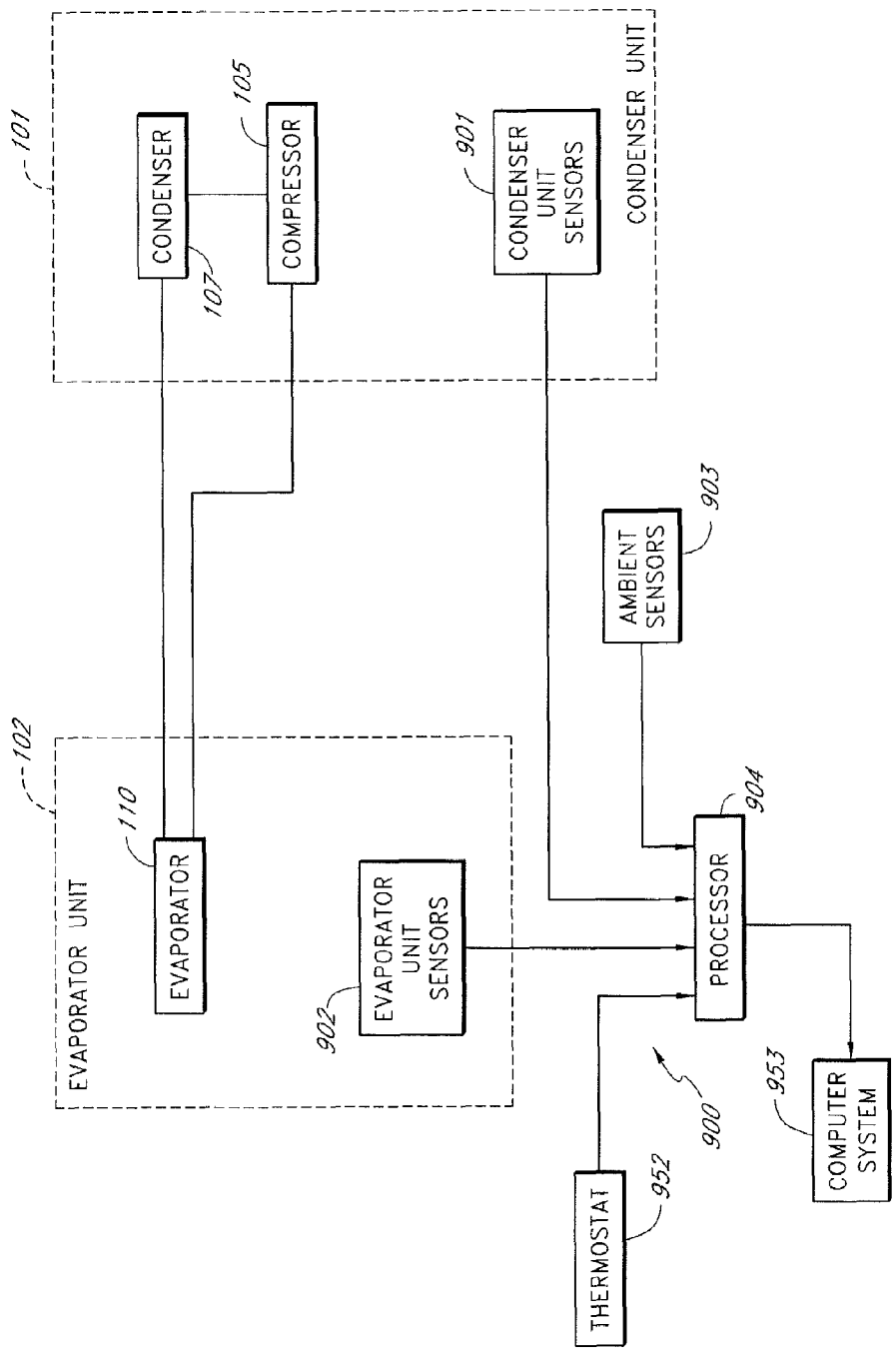
FIG. 9D is a block diagram of a monitoring system for monitoring the operation of the refrigerant-cycle system, where data regarding operation of the system is provided to a thermostat and/or to a computer system such as, for example, a site monitoring computer, a maintenance computer, a personal digital assistant, a personal computer, etc.

FIG. 9D is a block diagram of a monitoring system for monitoring the operation of the refrigerant-cycle system, where data regarding operation of the system is provided to a thermostat 952 and/or to a computer system 953 such as, for example, a site monitoring computer, a maintenance computer, a personal digital assistant, a personal computer, etc.

Figure 9E:
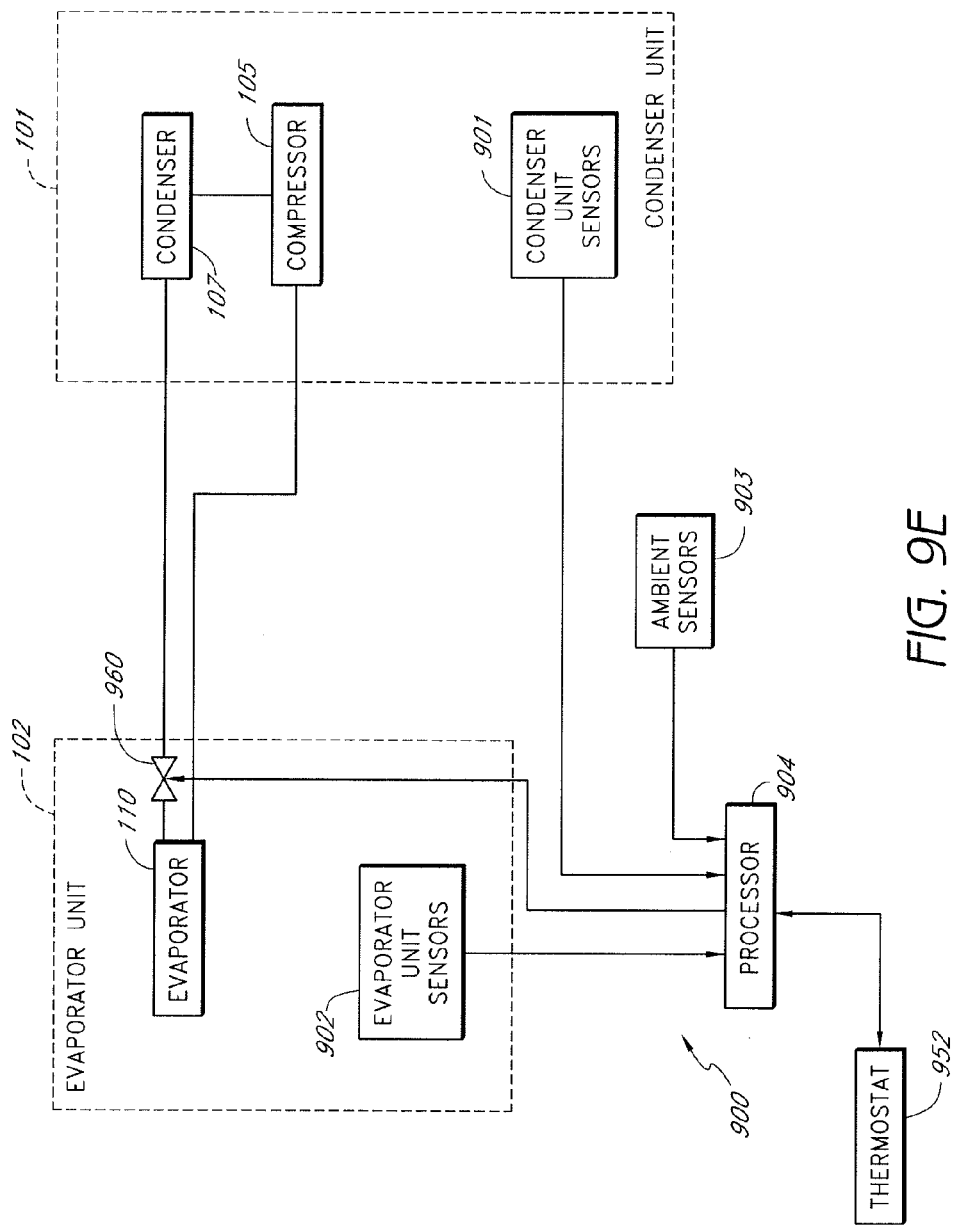
FIG. 9E is a block diagram of a monitoring system for monitoring the operation of the refrigerant-cycle system wherein an electronically-controlled metering device is provided to allow control of the system in an energy-efficient matter.

FIG. 9E is a block diagram of a monitoring system for monitoring the operation of the refrigerant-cycle system wherein an electronically-controlled metering device 960 is provided to allow control of the system in an energy-efficient matter.

Figure 9F:
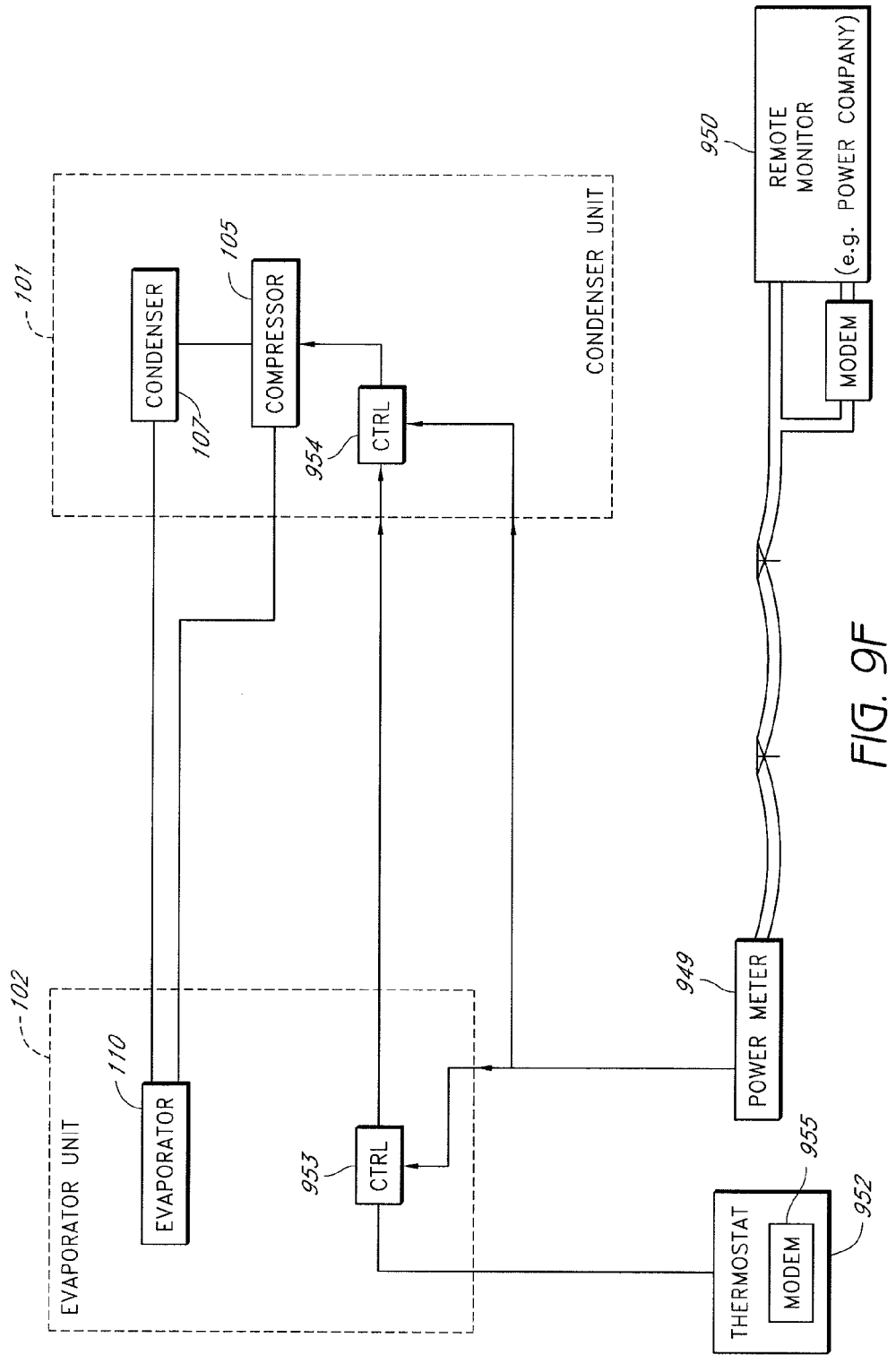
FIG. 9F is a block diagram of a thermostat control and monitoring system having a data interface device provided to the thermostat.

FIG. 9F is a block diagram of a thermostat control and monitoring system having a data interface device 955 provided to the thermostat 952. The thermostat 952 typically communicates with an evaporator unit controller 953 using relatively low-voltage control wiring. The control unit 953 typically provides relays and other control circuits for the air handler fan, and other systems in the evaporator unit 102. The control wiring is also provided to a condenser unit controller 954 in the condenser unit 101. The controller 954 provides relays and other control circuits for the compressor 105, the condenser fan, etc. The data interface device 955 is provided to the low-voltage control wiring to allow the thermostat 952 to receive control signals from the remote monitor 950.

Figure 9G:
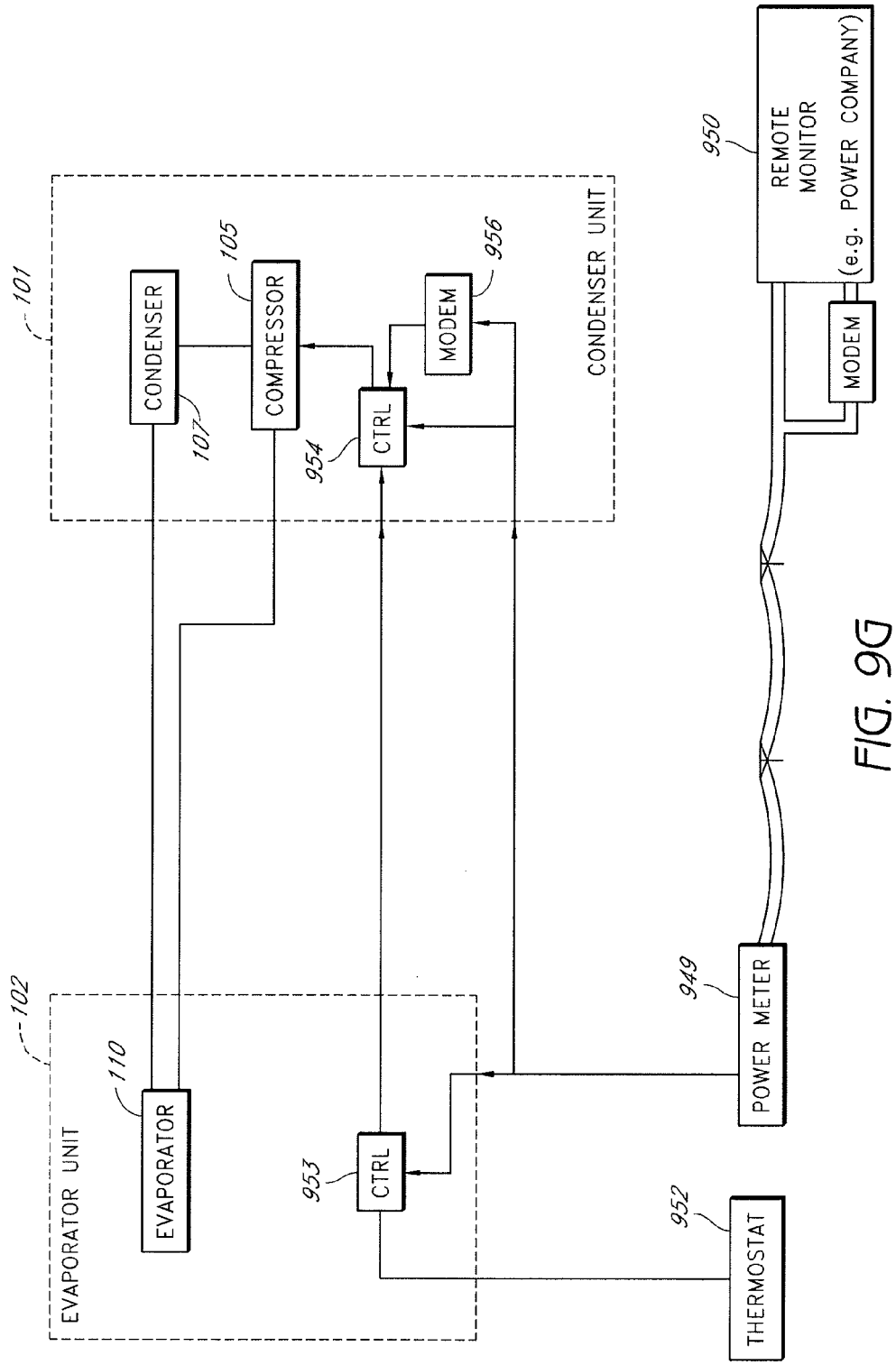
FIG. 9G is a block diagram of a thermostat control and monitoring system having a data interface device provided to the evaporator unit.

FIG. 9G is a block diagram of a thermostat control and monitoring system wherein a data interface device 956 is provided to the controller 954. The data interface device 956 allows the remote monitor 950 to communicate with the condenser unit. In one embodiment, the data interface device 956 allows the remote monitor to read sensor data from the condenser unit 101. In one embodiment, the data interface device 956 allows the remote monitor to turn off the condenser unit 101. In one embodiment, the data interface device 956 allows the remote monitor to switch the compressor 105 to a lower-speed mode. In one embodiment, the data interface device 956 allows the remote monitor to switch the condenser unit 101 to a power conservation mode.

Figure 9H:
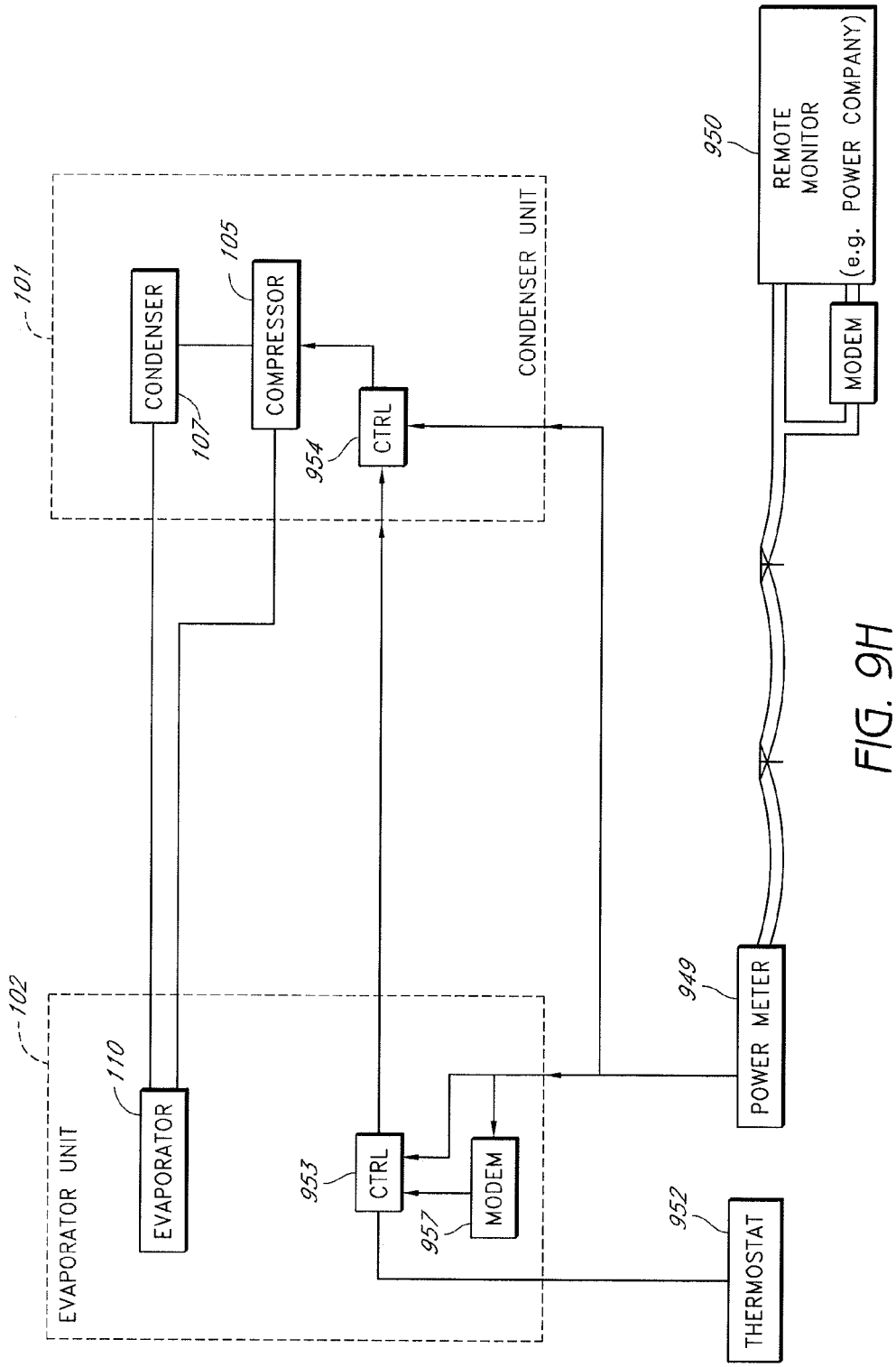
FIG. 9H is a block diagram of a thermostat control and monitoring system having a data interface device provided to the condenser unit.

FIG. 9H is a block diagram of a thermostat control and monitoring system wherein a data interface device 957 is provided to the controller 953.

In one embodiment, the data interface devices 955-957 are configured as power line modems (e.g., using Broadband over Power Line (BPL), or other power line networking technology). In one embodiment, the data interface devices 955-957 are configured as wireless modems for communication using wireless transmission. In one embodiment, the data interface devices 955-957 are configured as telephone modems, cable modems, Ethernet modems, or the like, to communicate using a wired network.

In one embodiment, the system 900 provides sensor data from the condenser unit sensors 901 and/or the evaporator unit sensors 902 to the remote monitoring service 950. In one embodiment, the system 900 uses data from the condenser unit sensors 901 and/or the evaporator unit sensors 902 to compute an efficiency factor for the refrigerant-cycle system and the system 900 provides the efficiency factor to the remote monitoring service 950. In one embodiment, the system 900 provides power usage data (e.g., amount of power used) by the refrigerant-cycle system and the system 900 provides the efficiency factor to the remote monitoring service 950. In one embodiment, the system 900 provides an identification code (ID) with the data transmitted to the remote monitor 950 to identify the system 900.

In one embodiment, the remote monitor 950 is provided with data regarding a maximum expected efficiency for the refrigerant-cycle system (e.g., based on the manufacture and design characteristics of the refrigerant-cycle system) such that the remote monitor 950 can ascertain the relative efficiency (that is, how the refrigerant-cycle system is operating with respect to its expected operating efficiency). In one embodiment, the remote monitor 950 provides efficiency data to the power company or to a government agency so electric rates can be charged according to the system efficiency. In one embodiment, the homeowner (or building owner) is charged a higher electrical rate for electrical power provided to a refrigerant-cycle system that is operating at a relatively low absolute efficiency. In one embodiment, the homeowner (or building owner) is charged a higher electrical rate for electrical power provided to a refrigerant-cycle system that is operating at a relatively low relative efficiency. In one embodiment, the homeowner (or building owner) is charged an electrical rate according to a combination the relative and absolute efficiency of the refrigerant-cycle system. In one embodiment, the data provided to the monitoring system 950 is used to provide notice to the homeowner (or building owner) that the refrigerant-cycle system is operating at a poor efficiency. In one embodiment, the data provided to the monitoring system 950 is used to provide notice to the homeowner (or building owner) that the refrigerant-cycle system is operating at a poor efficiency, and that the system must be serviced. In one embodiment, the owner is given a warning that service is needed. If the unit is not serviced (or if efficiency does not improve) after a period of time, the system 950 can remotely shut off the refrigerant-cycle system by sending commands to one or more of the interface devices 955-957.

In one embodiment, the homeowner (or building owner) is charged a higher electrical rate for electrical power provided to a refrigerant-cycle system that is operating at a relatively low efficiency during a specified period of time, such as, for example, when the power system is highly loaded, during peak afternoon cooling periods, during heat waves, during rolling blackouts, etc. In one embodiment, the homeowner (or building owner) is charged a higher electrical rate (a premium rate) for electrical power provided to a refrigerant-cycle system during a specified period of time, such as, for example, when the power system is highly loaded, during peak afternoon cooling periods, during heat waves, during rolling blackouts, etc. In one embodiment, the homeowner (or building owner) can programming the system 900 to receive messages from the power company indicating that premium rates are being charged. In one embodiment, the homeowner (or building owner) can program the system 900 to shut down during premium rate periods. In one embodiment, the homeowner (or building owner) can avoid paying premium rates by allowing the power company to remotely control operation of the refrigerant-cycle system during premium rate times. In one embodiment, the homeowner (or building owner) is only allowed to run the refrigerant-cycle system during premium rate periods if the system it operating above a prescribed efficiency.

In one embodiment, the system 900 monitors the amount of time that the refrigerant-cycle system has been running (e.g., the amount of runtime during the last day, week, etc.). In one embodiment, the remote monitoring system can query the system 900 to obtain data regarding the operating of the refrigerant-cycle system and one or more of the data interface devices 955-957 will receive the query and send the requested data to the monitoring system 950. The query data be, such as, for example, the efficiency rating of the refrigerant-cycle system (e.g., the SEER, EER, etc.), the current operating efficiency of the refrigerant-cycle system, the runtime of the system during a specified time period, etc. The system 950 operator (e.g., the power company or power transmission company), can use the query data to make load balancing decisions. Thus, for example the decision regarding whether to instruct the refrigerant-cycle system to shut down or go into a low power mode can be based on the system efficiency (specified efficiency, absolute efficiency, and/or relative efficiency), the amount of time the system has been running, the home or building owner's willingness to pay premium rates during load shedding periods, etc. Thus, for example a homeowner who has a low-efficiency system that is heavily used or who has indicated an unwillingness to pay premium rates, would have his/her refrigerant-cycle system shut off by the system 950 before that of a homeowner who has installed a high-efficiency system that is used relatively little, and who had indicated a willingness to pay premium rates. In one embodiment, in making the decision to shut off the system 900, the monitoring system 950 would take into account the efficiency of the system 900, the amount the system 900 is being used, and the owner's willingness to pay premium rates. In one embodiment, higher-efficiency systems are preferred over lower-efficiency systems (that is, higher-efficiency systems are less likely to be shut off during a power emergency), and lightly-used systems are preferred over heavily-used systems.

In one embodiment, the system 900 sends data regarding the set temperature of the thermostat 952 to the monitoring system 950. In one embodiment, the electricity rate charged to the homeowner (or building owner) calculated according to a set point of the thermostat 952 such that a lower set point results in a higher rate charge per kilowatt-hour. In one embodiment, the electricity rate charged to the homeowner (or building owner) calculated according to the set point of the thermostat 952 and the relative efficiency of the refrigerant-cycle system such that a lower set point and/or lower efficiency results in a higher rate charge per kilowatt-hour. In one embodiment, the electricity rate charged to the homeowner (or building owner) calculated according to the set point of the thermostat 952 and the absolute efficiency of the refrigerant-cycle system such that a lower set point and/or lower efficiency results in a higher rate charge per kilowatt-hour. In one embodiment, the electricity rate charged to the homeowner (or building owner) calculated according to the set point of the thermostat 952, the relative efficiency of the refrigerant-cycle system, and the absolute efficiency of the refrigerant-cycle system according to a formula whereby a lower set point and/or lower efficiency results in a higher rate charge per kilowatt-hour.

In one embodiment, the monitoring system 950 can send instructions to the system 900 to shut down if the refrigerant-cycle system is operating at a low efficiency. In one embodiment, the monitoring system 950 can send instructions to the system 900 to change the setting of the thermostat 952 (e.g., raise the set temperature of the thermostat 952) in response to low efficiency of the refrigerant-cycle system and/or to avoid a blackout. In one embodiment the monitoring system can send instructions to the condenser unit 101 to switch the compressor 105 to a low-speed mode to conserve power.

In one embodiment, the remote monitoring service knows the identification codes or addresses of the data interface devices 955-957 and correlates the identification codes with a database to determine whether the refrigerant-cycle system is serving a relatively high priority client such as, for example, a hospital, the home of an elderly or invalid person, etc. In such circumstances, the remote monitoring system can provide relatively less cutback in cooling provided by the refrigerant-cycle system.

In one embodiment, the system 900 communicates with the monitoring system 950 to provide load shedding. Thus, for example, the monitoring system (e.g., a power company) can communicate with the data interface device 956 and/or the data interface device 957 to turn off the refrigerant cycle system. The monitoring system 950 can thus rotate the on and off times of air conditioners across a region to reduce the power load without implementing rolling blackouts. In one embodiment, the data interface device 956 is configured as a retrofit device that can be installed in a condenser unit to provide remote shutdown. In one embodiment, the data interface device 956 is configured as a retrofit device that can be installed in a condenser unit to remotely switch the condenser-unit to a low power (e.g., energy conservation) mode. In one embodiment, the data interface device 957 is configured as a retrofit device that can be installed in an evaporator unit to provide remote shutdown or to remotely switch the system to a lower power mode. In one embodiment, the remote system 950 sends separate shutdown and restart commands to one or more of the data interface devices 955-957. In one embodiment, the remote system 950 sends commands to the data interface devices 955-957 to shutdown for a specified period of time (e.g., 10 min, 30 min, 1 hour, etc.) after which the system automatically restarts.

In one embodiment, the system 900 communicates with the monitoring system 950 to control the temperature set point of the thermostat 952 to prevent blackouts or brownouts without regard to efficiency of the refrigerant-cycle system. When brownout or potential blackout conditions occur, the system 950 can override the homeowner's thermostat setting to cause the temperature set point on the thermostat 952 to change (e.g. increase) in order to reduce power usage. In most residential installations, low-voltage control wiring is provided between the thermostat 952 and the evaporator unit 102 and condenser unit 101. In most residential (and many industrial) applications the thermostat 952 receives electrical power via the low-voltage control wiring from a step-down transformer provided with the evaporator unit 102.

In one embodiment, the modem 955 is provided in connection with the power meter 949, and the modem 955 communicates with the thermostat 952 using wireless communications.

In a typical refrigeration or air conditioning system, the condenser unit 101 is placed outside the area being cooled and the evaporator unit 102 is placed inside the area being cooled. The nature of outside and inside depend on the particular installation. For example, in an air conditioning or HVAC system, the condenser unit 101 is typically placed outside the building, and the evaporator unit 102 is typically placed inside the building. In a refrigerator or freezer, the condenser unit 101 is placed outside the refrigerator and the evaporator unit 102 is placed inside the refrigerator. In any case, the waste heat from the condenser should be dumped outside (e.g., away from) the area being cooled.

When the system 900 is installed, the system 900 is programmed by specifying the type of refrigerant used, and the characteristics of the condenser 107, the compressor 105, and the evaporator unit 102. In one embodiment, the system 900 is also programmed by specifying the size of the air handler system. In one embodiment, the system 900 is also programmed by specifying the expected (e.g., design) efficiency of the system 100.

The monitoring system can do a better job of monitoring efficiency that published performance ratings such as the Energy Efficiency Ratio (EER) and SEER. The EER is determined by dividing the published steady state capacity by the published steady sate power input at 80° F. dB/67° F. Wb indoor and 95° F. dB outdoor. This is objective yet unrealistic with respect to system "real world" operating conditions. The published SEER rating of a system is determined by multiplying the steady state EER measured at conditions of 82° F. outdoor temperature, 80° F. dB/67° F. Wb indoor entering air temperature by the (run time) Part Load Factor (PLF) of the system. A major factor not considered in SEER calculation is the actual part loading factor of the indoor evaporator cooling coil, which reduces the unit's listed BTUH capacity and SEER efficiency level. Many older air handlers and duct systems, do not deliver the published BTUH and SEER Ratings. This is primarily due to inadequate air flow through the evaporator 110, a dirty evaporator 110, and/or dirty blower wheels. Also, improper location of supply diffusers and return air registers can result in inefficient floor level recirculation of the cold conditioned air, resulting in lack of heat loading of the evaporator 110.

By monitoring the system under actual load conditions, and by measuring the relevant ambient temperature and humidity, the system 900 can calculate the actual efficiency of the system 100 in operation.

Figures 10, 10A:
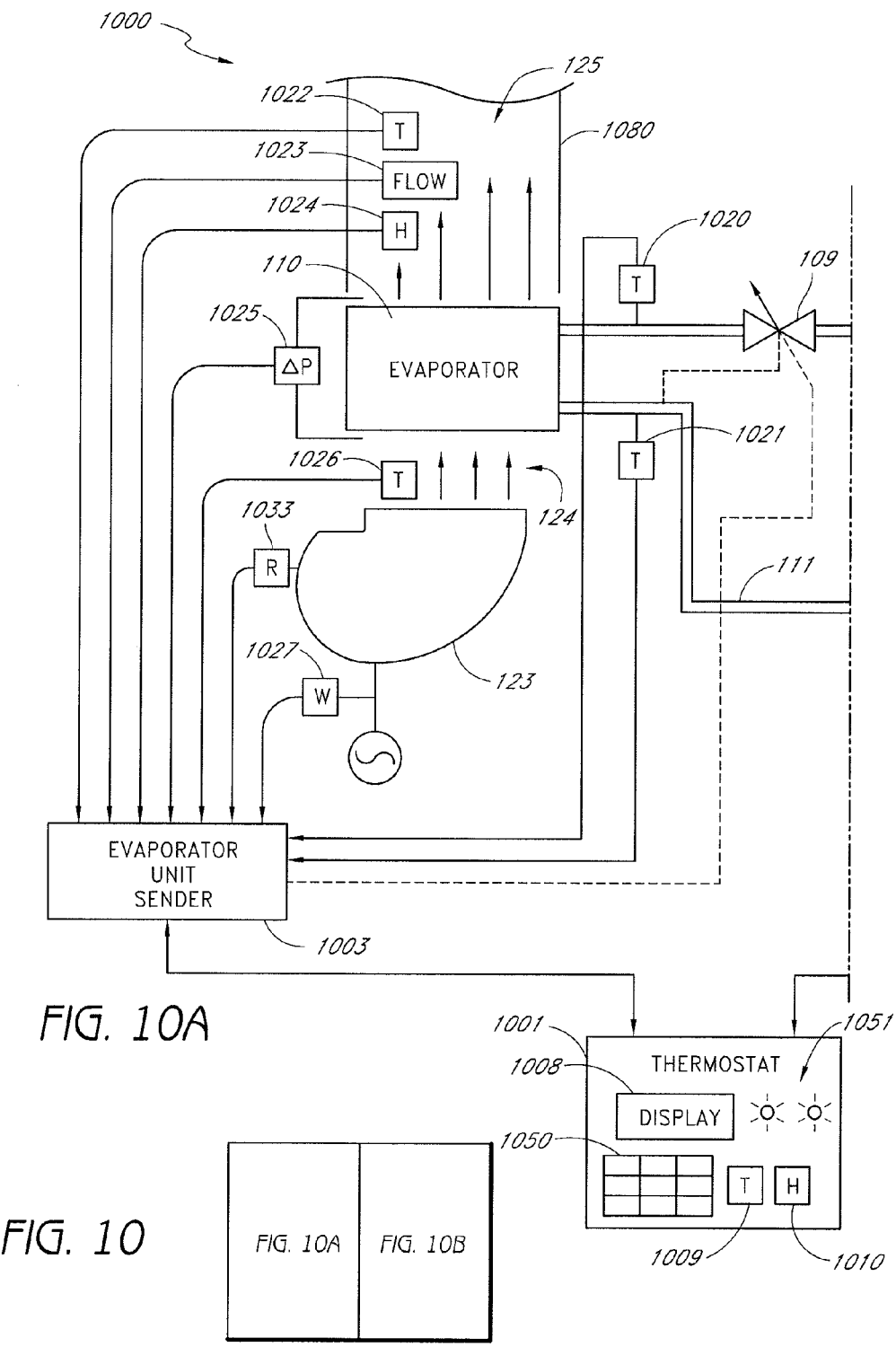
FIG. 10 (consisting of FIGS. 10A and 10B) shows various sensors that can be used in connection with the system of FIGS. 9A-H for monitoring the operation of the refrigerant-cycle system.
Figure 10B:
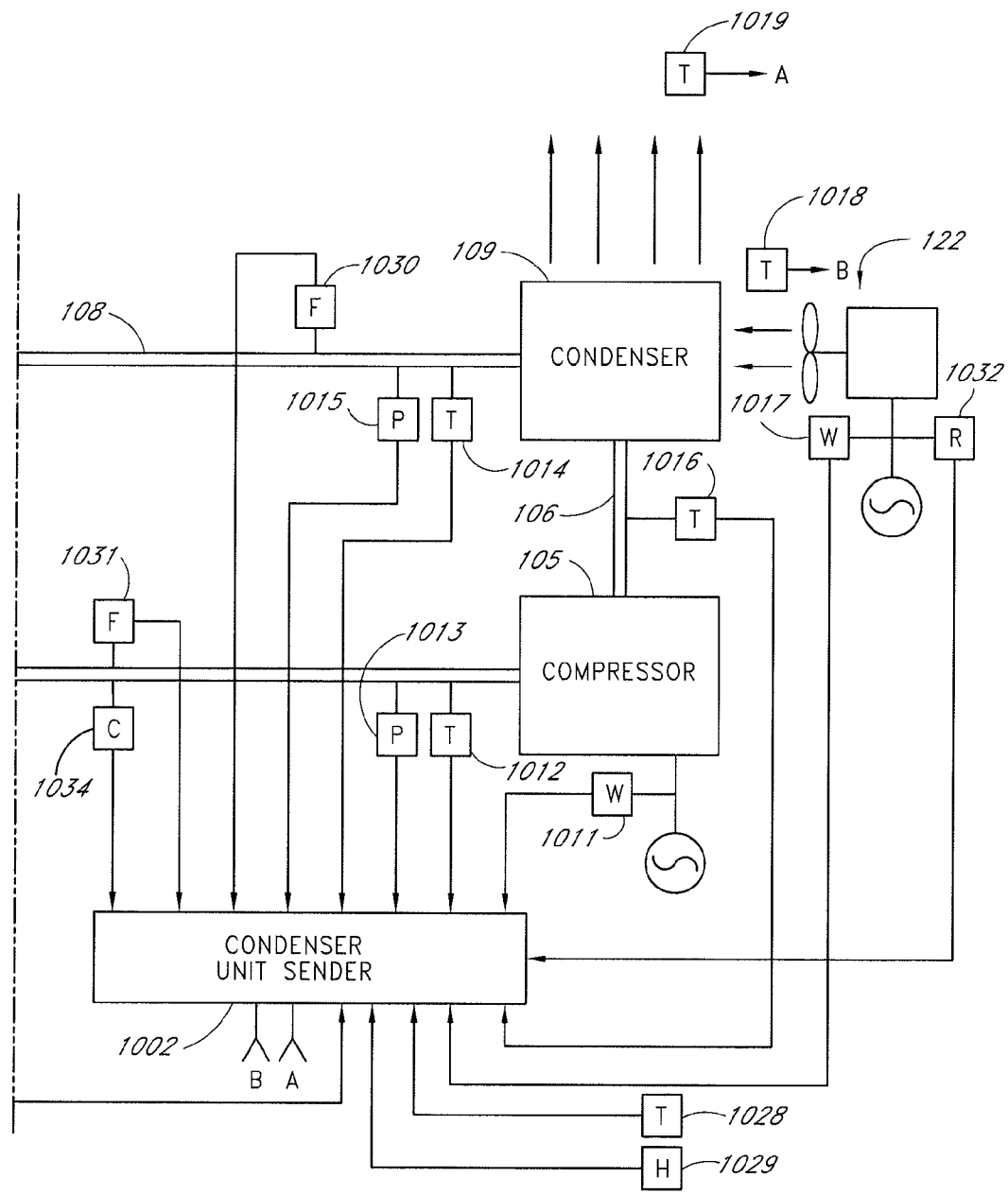

FIG. 10 shows a monitoring system 1000 for monitoring the operation of the refrigerant-cycle system 100. The system 1000 shown in FIG. 10 is one example of an embodiment of the system 900 shown in FIGS. 9A-E. In the system 1000, a condenser unit sender 1002 monitors operation of the condenser unit 101 through one or more sensors, a evaporator sender unit 1003 monitors operation of the evaporator unit 102 through one or more sensors. The condenser unit sender 1002 and the sender unit 1003 communicate with the thermostat 1001 to provide data to the building owner. For purposes of explanation, and not by way of limitation, in FIG. 10 the processor 904 and thermostat 952 from FIGS. 9A-E are shown as a single thermostat-processor. One of ordinary skill in the art will recognize that the processor functions can be separated from the thermostat.

In one embodiment, a building interior temperature sensor 1009 is provided to the thermostat 101. In one embodiment, a building interior humidity sensor 1010 is provided to the thermostat 101. In one embodiment, the thermostat 1001 includes a display 1008 for displaying system status and efficiency. In one embodiment, the thermostat 1001 includes a keypad 1050 and/or indicator lights (e.g., LEDs) 1051. A power sensor 1011 to sense electrical power consumed by the compressor 105 is provided to the condenser unit sender 1002. In one embodiment, a power sensor 1017 to sense electrical power consumed by the condenser fan 122 is provided to the condenser unit sender 1002. The air 125 from the evaporator 110 flows in the ductwork 1080.

In one embodiment, a temperature sensor 1012, configured to measure the temperature of the refrigerant in the suction line 111 near the compressor 105, is provided to the condenser unit sender 1002. In one embodiment, a temperature sensor 1016, configured to measure the temperature of the refrigerant in the hot gas line 106, is provided to the condenser unit sender 1002. In one embodiment, a temperature sensor 1014, configured to measure the temperature of the refrigerant in the fluid line 108 near the condenser 107, is provided to the condenser unit sender 1002.

Contaminants in the refrigerant lines 111, 106, 108, etc. can reduce the efficiency of the refrigerant-cycle system and can reduce the life of the compressor or other system components. In one embodiment, one or more contaminant sensors 1034, configured to sense contaminants in the refrigerant (e.g., water, oxygen, nitrogen, air, improper oil, etc.) are provided in at least one of the refrigerant lines and provided to the condenser unit sender 1002 (or, optionally, to the evaporator unit sender 1003). In one embodiment, the contaminant sensor 1060 senses refrigerant fluid or droplets at the input to the compressor 105, which can cause damage to the compressor 105. In one embodiment, a contaminant sensor 1060 is provided in the liquid line 108 to sense bubbles in the refrigerant. Bubbles in the liquid line 106 may indicate low refrigerant levels, an undersized condenser 109, insufficient cooling of the condenser 109, etc. In one embodiment, the sensor 1034 senses water or water vapor in the refrigerant lines. In one embodiment, the sensor 1034 senses acid in the refrigerant lines. In one embodiment, the sensor 1034 senses acid in the refrigerant lines. In one embodiment, the sensor 1034 senses air or other gasses (e.g., oxygen, nitrogen, carbon dioxide, chlorine, etc.).

In one embodiment, a pressure sensor 1013, configured to measure pressure in the suction line 111, is provided to the condenser unit sender 1002. In one embodiment, a pressure sensor 1015, configured to measure pressure in the liquid line 108, is provided to the condenser unit sender 1002. In one embodiment, a pressure sensor (not shown), configured to measure pressure in the hot gas line 106, is provided to the condenser unit sender 1002. In one embodiment, the pressure sensor 1013 and the pressure sensor 1015 are connected to the system 100, by attaching the pressure sensors 1013 and 1015 to the service valves 120 and 121, respectively. Attaching the pressure sensors to the pressure valves is a convenient way to access refrigerant pressure in a retrofit installation without having to open the pressurized refrigerant system.

In one embodiment, a flow sensor 1031, configured to measure flow in the suction line 111, is provided to the condenser unit sender 1002. In one embodiment, a flow sensor 1030, configured to measure flow in the liquid line 108, is provided to the condenser unit sender 1002. In one embodiment, a flow sensor (not shown), configured to measure flow in the hot gas line 106, is provided to the condenser unit sender 1002. In one embodiment, the flow sensors are ultrasonic sensors that can be attached to the refrigerant lines without opening the pressurized refrigerant system.

In one embodiment, a temperature sensor 1028 configured to measure ambient temperature is provided to the condenser unit sender 1002. In one embodiment, a humidity sensor 1029 configured to measure ambient humidity is provided to the condenser unit sender 1002.

In one embodiment, a temperature sensor 1020, configured to measure the temperature of the refrigerant in the liquid line 108 near the evaporator 110 is provided to the sender unit 1003. In one embodiment, a temperature sensor 1021, configured to measure the temperature of the refrigerant in the suction line 111 near the evaporator 110 is provided to the sender unit 1003.

In one embodiment, a temperature sensor 1026, configured to measure the temperature of air 124 flowing into the evaporator 110 is provided to the sender unit 1003.

In one embodiment, a temperature sensor 1026, configured to measure the temperature of air 125 flowing out of the evaporator 110 is provided to the sender unit 1003. In one embodiment, a flow sensor 1023, configured to measure the airflow of air 125 flowing out of the evaporator 110 is provided to the sender unit 1003. In one embodiment, a humidity sensor 1024, configured to measure the temperature of air 125 flowing out of the evaporator 110 is provided to the sender unit 1003. In one embodiment, a differential pressure sensor 1025, configured to measure a pressure drop across the evaporator 110, is provided to the sender unit 1003.

In one embodiment, the temperature sensors are attached to the refrigerant lines (e.g., the lines 106, 108, 111, in order to measure the temperature of the refrigerant circulating inside the lines. In one embodiment, the temperature sensors 1012 and/or 1016 are provided inside the compressor 105. In one embodiment, the temperature sensors are provided inside one or more of the refrigerant lines.

A tachometer 1033 senses rotational speed of the fan blades in the fan 123. The tachometer is provided to the evaporator unit sender 1003. A tachometer 1032 senses rotational speed of the fan blades in the condenser fan 122. The tachometer 1032 is provided to the condenser unit sender 1002.

In one embodiment, a power sensor 1027, configured to measure electrical power consumed by the fan 123 is provided to the sender unit 1003.

In one embodiment, the sender unit 1003 communicates sensor data to the condenser unit sender 1002 through wireless transmission. In one embodiment, the sender unit 1003 communicates sensor data to the condenser unit sender 1002 through existing HVAC wiring. In one embodiment, the sender unit 1003 communicates sensor data to the condenser unit sender 1002 through existing HVAC wiring by modulating sensor data onto a carrier that is transmitted using the existing HVAC wiring.

Each of the sensors shown in FIG. 10 (e.g., the sensors 1010-1034 etc.) are optional. The system 1000 can be configured with a subset of the illustrated sensors in order to reduce cost at the expense of monitoring system capability. Thus, for example, the contaminant sensors 1034 can be eliminated, but ability of the system 1000 to detect the contaminants sensed by the sensor 1034 will be compromised or lost.

The pressure sensors 1013 and 1015 measure suction and discharge pressures, respectively, at the compressor 105. The temperature sensors 1026 and 1022 measure evaporator 110 supply air and return air, respectively. The temperature sensors 1018 and 1019 measure input air and discharge air, respectively, at the condenser 107.

The power sensors 1011, 1017, and 1027 are configured to measure electric power. In one embodiment, one or more of the power sensors measure voltage provided to a load and power is computed by using a specified impedance for the load. In one embodiment, one or more of the power sensors measure current provided to a load and power is computed by using a specified impedance for the load. In one embodiment, one or more of the power sensors measure voltage and current provided to a load and power is computed by using a specified power factor for the load. In one embodiment, the power sensors measure voltage, current, and the phase relationship between the voltage and the current.

The temperature sensors 1012 and/or 1021 measure the temperature of the refrigerant at the suction line 111. By measuring the suction line 111 temperature, the superheat can be determined. The suction pressure has been measured by the pressure sensor 1013, the evaporating temperature can be read from a pressure-temperature chart. The superheat is the difference between the suction line 111 temperature and the evaporating temperature.

The temperature sensors 1014 and/or 1020 measure the temperature of the refrigerant in the liquid line 108. By measuring the liquid line 108 temperature, the subcooling can be determined. The discharge pressure is measured by the pressure sensor 1015, and thus the condensing temperature can be read from the pressure-temperature chart. The subcooling is the difference between the liquid line 108 temperature and the condensing temperature.

In one embodiment, the system 1000 calculates efficiency by measuring the work (cooling) done by the refrigerant-cycle system and dividing by the power consumed by the system. In one embodiment, the system 1000 monitors the system for abnormal operation. Thus, for example, in one embodiment, the system 1000 measures the refrigerant temperature drop across the condenser 109 using the temperature sensors 1016 and 1014 to be used in calculating the heat removed by the condenser. The system 1000 measures the refrigerant temperature drop across the evaporator 110 to be used in calculating the heat absorbed by the evaporator 110.

The monitoring system is typically used to monitor the operation of a system 100 that was originally checked out and put into proper operation condition. Mechanical problems in an air conditioning system are generally classified in two categories: air side problems and refrigeration side problems.

The primary problem that can occur in the air category is a reduction in airflow. Air handling systems do not suddenly increase in capacity, that is, increase the amount of air across the coil. On the other hand, the refrigeration system does not suddenly increase in heat transfer ability. The system 1000 uses the temperature sensors 1026 and 1022 to measure the temperature drop of the air through the evaporator 110. After measuring the return air and supply air temperatures and subtracting to get the temperature drop, the system 1000 checks to see whether the temperature difference higher or lower than it should be.

Figure 11:
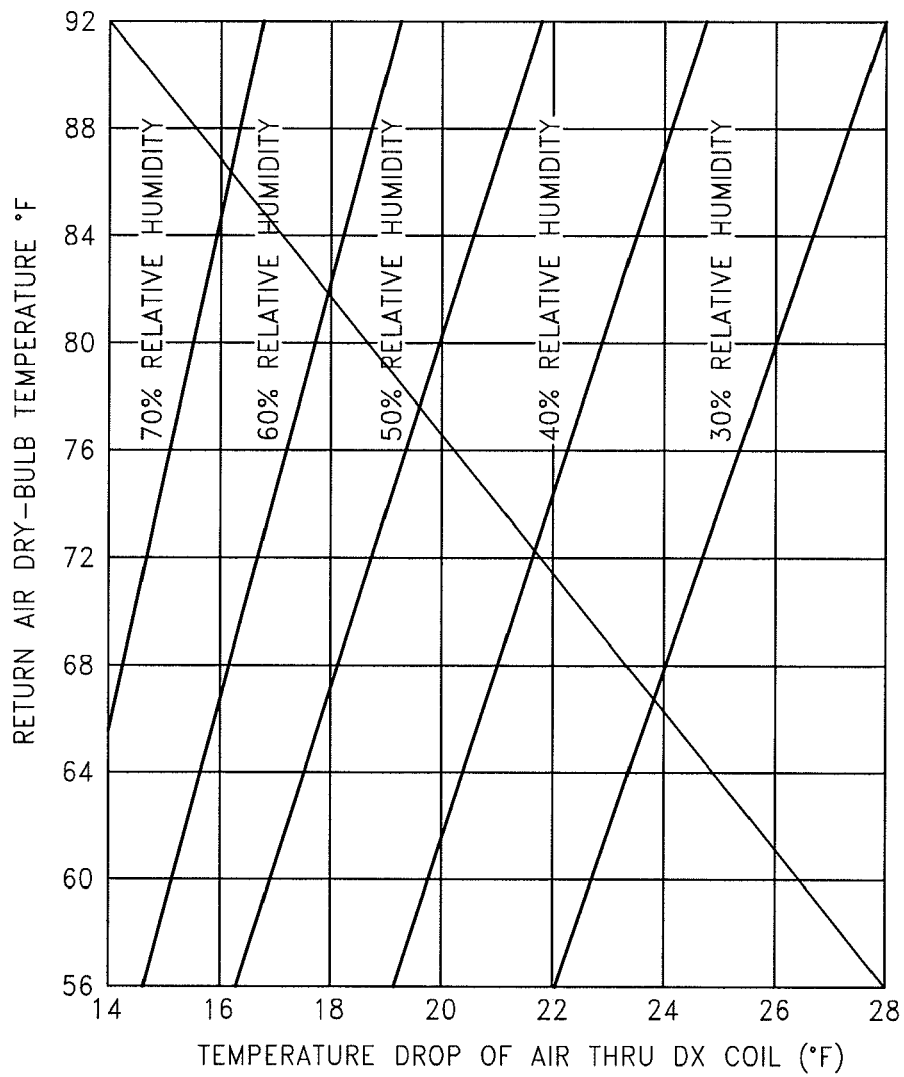
FIG. 11 shows the temperature drop across in the air through the evaporator as a function of humidity.

FIG. 11 shows the temperature drop across in the air through the evaporator as a function of humidity. In one embodiment, the humidity sensors 1024 and/Or 1041 are used to measure building humidity, and/or the humidity sensor 1041 is used to measure ambient humidity. The humidity readings are used to correct temperature readings for wet bulb temperature according to relative humidity.

In one embodiment, a comparison of the desired (or expected) temperature drop across the evaporator 110 with the measured actual temperature drop, is used to help classify potential air problems from refrigerant-cycle problems. If the actual temperature drop is less than the required temperature drop, then the airflow has likely been reduced. Reduced airflow can be caused by dirty air filters or evaporator 110, problems with the fan 123, and/or unusual restrictions in the duct system.

Air filters of the throwaway type are typically replaced at least twice each year, at the beginning of both the cooling and heating seasons. In one embodiment, the thermostat allows the owner to indicate when a new air filter is installed. The thermostat keeps track of the time the filter has been in use, and provides a reminder to the owner when the filter should be replaced. In one embodiment, the thermostat uses actual elapsed clock time to determine filter usage.

In one embodiment, the thermostat 1001 calculates filter usage according to the amount of time the air handler has been blowing air through the filter. Thus, for example, in moderate climates or seasons where the air handler system is not used continuously, the thermostat will wait a longer period of actual time before indicating that filter replacement is warranted. In some areas of higher use or where dust is high, the filter will generally have to be replaced relatively more often. In one embodiment, the thermostat uses a weighting factor to combine running time with idle time to determine filter usage. Thus, for example, in determining filter usage, hours when the hair handler is blowing air thorough the filter are weighted relatively more heavily than hours where the air handler system is idle. In one embodiment, the owner can program the thermostat to indicate that filter replacement is needed after a specified number of hours or days (e.g., as actual days, as running days, or as a combination thereof).

In one embodiment, the thermostat 1001 is configured to receive information from an information source regarding daily atmospheric dust conditions and to use such information in calculating filter usage. Thus, in one embodiment, when calculating filter use, the thermostat weighs days of relatively high atmospheric dust relatively more heavily than days of relatively low atmospheric dust. In one embodiment, the information source for atmospheric dust information includes a data network, such as, for example, the Internet, a pager network, a local area network, etc.

In one embodiment, the thermostat collects data for calculating filter usage and passes such data to a computer monitoring system.

In commercial and industrial applications, a regular schedule of maintenance is generally used. In one embodiment, sensors are provided in connection with the air filter, as described below in connection with FIG. 11.

In one embodiment, power measured by the power meter 1027 is used to help diagnose and detect problems with the blower 123 and/or the air handler system. If the blower 123 is drawing too much or too little current, or if the blower 123 is showing a low power factor, then possible problems with the blower and/or air handler system are indicated.

Placing furniture or carpeting over return air grilles reduces the air available for the blower to handle. Shutting off the air to unused areas will reduce the air over the evaporator 110. Covering a return air grille to reduce the noise from the centrally located furnace or air handler may reduce the objectionable noise, but it also drastically affects the operation of the system by reducing the air quantity. The collapse of the return air duct system will affect the entire duct system performance. Air leaks in the return duct will raise the return air temperature and reduce the temperature drop across the coil.

The air flow sensor 1023 can be used to measure air flow through the ducts. In one embodiment, the air flow sensor 1023 is a hot wire (or hot film) mass flow sensor. In one embodiment, the differential pressure sensor 1025 is used to measure airflow through the evaporator 110. In one embodiment, the differential pressure sensor 1025 is used to measure drop across the evaporator 110. In one embodiment, the pressure drop across the evaporator is used to estimate when the evaporator 110 is restricting airflow (e.g., due to damage, dirt, hair, dust, etc.). In one embodiment, the differential pressure sensor 1025 is used to measure drop across an air filter to estimate when the filter is restricting airflow (e.g., due to age, damage, dirt, hair, dust, etc.). In one embodiment, the indicator lights 1051 are used to indicate that the filter needs to be changed. In one embodiment, the indicator lights 1051 are used to indicate that the evaporator 110 needs to be cleaned.

In one embodiment, the airflow sensor 1023 is used to measure airflow into the ductwork 1080. In one embodiment, the indicator lights 1051 are used to indicate that the airflow into the ductwork 1080 is restricted (e.g., due to dirt, furniture or carpets placed in front of vents, closed vents, dirty evaporator, dirty fan blades, etc.).

In one embodiment, a dust sensor is provided in the air stream of the evaporator 110. In one embodiment, the dust sensor includes a light source (optical and/or infrared) and a light sensor. The dust sensor measures light transmission between the source and the light sensor. The buildup of dust will cause the light to be attenuated. The sensor detects the presence of dust buildup at the evaporator 110 by measuring light attenuation between the light source and the light sensor. When the attenuation exceeds a desired value, the monitoring system 1000 indicates that cleaning of the air flow system is needed (e.g., the fan 123, the duct work 1080, and/or the evaporator 110, etc.).

In one embodiment, the power sensor 1027 is used to measure power provided to the blower motor in the fan 123. If the fan 123 is drawing too much power or too little power, then potential airflow problems are indicated (e.g., blocked or closed vents, dirty fan blades, dirty evaporator, dirty filter, broken fan belt, slipping fan belt, etc.).

If the temperature drop across the evaporator 1010 is less than desired, then the heat removal capacity of the system has been reduced. Such problems can generally be divided into two categories: refrigerant quantity, and refrigerant flow rate. If the system 100 has the correct amount of refrigerant charge and refrigerant is flowing at the desired rate (e.g., as measured by the flow sensors 1031 and/or 1030), the system should work efficiently and deliver rated capacity. Problems with refrigerant quantity or flow rate typically affect the temperatures and pressures that occur in the refrigerant-cycle system when the correct amount of air is supplied through the evaporator 110. If the system is empty of refrigerant, a leak has occurred, and it must be found and repaired. If the system will not operate at all, it is probably an electrical problem that must be found and corrected.

If the system 100 will start and run but does not produce satisfactory cooling, then the amount of heat picked up in the evaporator 110 plus the amount of motor heat added and the total rejected from the condenser 107 is not the total heat quantity the unit is designed to handle. To diagnose the problem, the information listed in Table 1 is used. These results compared to normal operating results will generally identify the problem: (1) Evaporator 110 operating temperature; (2) Condensing unit condensing temperature; and/or (3) Refrigerant subcooling.

These items can be modified according to the expected energy efficiency ratio (EER) of the unit. The amount of evaporation and condensing surface designed into the unit are the main factors in the efficiency rating. A larger condensing surface results in a lower condensing temperature and a higher EER. A larger evaporating surface results in a higher suction pressure and a higher EER. The energy efficiency ratio for the conditions is calculated by dividing the net capacity of the unit in Btu/hr by the watts input.

Normal evaporator 110 operating temperatures can be found by subtracting the design coil split from the average air temperature going through the evaporator 110. The coil split will vary with the system design. Systems in the EER range of 7.0 to 8.0 typically have design splits in the range 25 to 30° F. Systems in the EER range of 8.0 to 9.0 typically have design splits in the range 20 to 25° F. Systems with 9.0+EER ratings will have design splits in the range 15 to 20° F. The formula used for determining coil operating temperatures is:

$$COT = \left(\frac{EAT + LAT}{2}\right) - \text{split}$$

where COT is the coil operating temperature, EAT is the entering air temperature of the coil (e.g., as measured by the temperature sensor 1026), LAT is the leaving air temperature of the coil (e.g., as measured by the temperature sensor 1022), and split is the design split temperature.

The value (EAT+LAT)/2 is the average air temperature, which is also referred to as the mean temperature difference (MTD). It is also sometimes referred to as the coil TED or ΔT.

"Split" is the design split according to the EER rating. For example, a unit having an entering air condition of 80° DB and a 20° F. temperature drop across the evaporator 110 coil will have an operating coil temperature determined as follows: For an EER rating of 7.0 of 8.0:

$$COT = \left(\frac{80 + 60}{2}\right) - 25 \text{ to } 30° = 40 \text{ to } 45° \text{ F.}$$

For an EER rating of 8.0 to 9.0:

$$COT = \left(\frac{80 + 60}{2}\right) - 20 \text{ to } 25° = 45 \text{ to } 50° \text{ F.}$$

TABLE 1

| Probable Cause | Suction Pressure (psig) | Evaporator Superheat (° F.) | Hot Gas Pressure (psig) | Condenser Liquid Subcooling (° F.) | Compressor Current (A) |
|---|---|---|---|---|---|
| 1. Insufficient or unbalanced load | Low | Low | Low | Normal | Low |
| 2. Excessive load | High | High | High | Normal | High |
| 3. Low ambient temperature | Low | High | Low | Normal | Low |
| 4. High ambient temperature | High | High | High | Normal | High |
| 5. Refrigerant undercharge | Low | High | Low | Low | Low |
| 6. Refrigerant overcharge | High | Low | High | High | High |
| 7. Liquid line restriction | Low | High | Low | High | Low |
| 8. Plugged capillary tube | Low | High | High | High | Low |
| 9. Suction line restriction | Low | High | Low | Normal | Low |
| 10. Hot gas line restriction | High | High | High | Normal | High |
| 11. Inefficient compressor | High | High | Low | Low | Low |

For an EER rating of 9.0+:

$$COT = \left(\frac{80+60}{2}\right) - 15 \text{ to } 20° = 50 \text{ to } 55° \text{ F.}$$

Thus, the operating coil temperature changes with the EER rating of the unit.

The surface area of the condenser 107 affects the condensing temperature the system 100 must develop to operate at rated capacity. The variation in the size of the condenser 107 also affects the production cost and price of the unit. The smaller the condenser 107, the lower the efficiency (EER) rating. In the same EER ratings used for the evaporator 110, at 95° F. outside ambient, the 7.0 to 8.0 EER category will operate in the 25 to 30° condenser 107 split range, the 8.0 to 9.0 EER category in the 20 to 25° condenser 107 split range, and the 9.0+ EER category in the 20 to 25° condenser 107 split range, and the 9.0+ EER category in the 15 to 20° condenser 107 split range.

This means that when the air entering the condenser 107 is at 95° F., the formula for finding the condensing temperature is:

$$RCT = EAT + \text{split}$$

where RCT is the refrigerant condensing temperature, EAT is the entering air temperature of the condenser 107, and split is the design temperature difference between the entering air temperature and the condensing temperatures of the hot high pressure vapor from the compressor 105.

For example, using the formula with 95° F. EAT, the split for the various EER systems would be:

For an EER rating of 7.0 to 8.0

$$RCT = 95° + 25 \text{ to } 30° = 120 \text{ to } 125° \text{ F.}$$

For an EER rating of 8.0 to 9.0

$$RCT = 95° + 20 \text{ to } 25° = 115 \text{ to } 120° \text{ F.}$$

For an EER rating of 9.0+

$$RCT = 95° + 15 \text{ to } 20° = 110 \text{ to } 115° \text{ F.}$$

The operating head pressures vary not only from changes in outdoor temperatures but with the different EER ratings.

The amount of subcooling produced in the condenser 107 is determined primarily by the quantity of refrigerant in the system. The temperature of the air entering the condenser 107 and the load in the evaporator 110 will have only a relatively small effect on the amount of subcooling produced. The amount of refrigerant in the system has the predominant effect. Therefore, regardless of EER ratings, the unit should have, if properly charged, a liquid subcooled to 15 to 20° F. High ambient temperatures will produce the lower subcooled liquid because of the reduced quantity of refrigerant in the liquid state in the system. More refrigerant will stay in the vapor state to produce the higher pressure and condensing temperatures needed to eject the required amount of heat.

Table 1 shows 11 probable causes of trouble in an air conditioning system. After each probable cause is the reaction that the cause would have on the refrigeration system low side or suction pressure, the evaporator 110 superheat, the high side or discharge pressure, the amount of subcooling of the liquid leaving the condenser 107, and the amperage draw of the condensing unit. In one embodiment, an airflow sensor (not shown) is included to measure the air over the condenser.

Insufficient air over the evaporator 110 (as measured, for example, by using the airflow sensor 1023 and/or the differential pressure sensor 1025) is indicated by a greater than desired temperature drop in the air through the evaporator 110. An unbalanced load on the evaporator 110 will also give the opposite indication, indicating that some of the circuits of the evaporator 110 are overloaded while others are lightly loaded. In one embodiment, the temperature sensor 1022 includes multiple sensors to measure the temperature across the evaporator. The lightly loaded sections of the evaporator 110 allow liquid refrigerant to leave the coil and enter the suction manifold and suction line.

In TXV systems, the liquid refrigerant passing the sensing bulb of the TXV can cause the valve to close down. This reduces the operating temperature and capacity of the evaporator 110 as well as lowering the suction pressure. The evaporator 110 operating superheat can become very low because of the liquid leaving some of the sections of the evaporator 110.

With inadequate airflow, high side or discharge pressure will be low due to the reduced load on the compressor 105, reduced amount of refrigerant vapor pumped, and reduced heat load on the condenser 107. Condenser 107 liquid subcooling would be on the high side of the normal range because of the reduction in refrigerant demand by the TXV. Condensing unit amperage draw would be down due to the reduced load.

In systems using fixed metering devices, the unbalanced load would produce a lower temperature drop of the air through the evaporator 110 because the amount of refrigerant supplied by the fixed metering device would not be reduced; therefore, the system pressure (boiling point) would be approximately the same.

The evaporator 110 superheat would drop to zero with liquid refrigerant flooding into the suction line. Under extreme case of imbalance, liquid returning to the compressor 105 could cause damage to the compressor 105. The reduction in heat gathered in the evaporator 110 and the lowering of the refrigerant vapor to the compressor 105 will lower the load on the compressor 105. The compressor 105 discharge pressure (hot gas pressure) will be reduced.

The flow rate of the refrigerant will be only slightly reduced because of the lower head pressure. The subcooling of the refrigerant will be in the normal range. The amperage draw of the condensing unit will be slightly lower because of the reduced load on the compressor 105 and reduction in head pressure.

In the case of excessive load, the opposite effect exists. The temperature drop of the air through the coli will be less, because the unit cannot cool the air as much as it should. Air is moving through the coil at too high a velocity. There is also the possibility that the temperature of the air entering the coil is higher than the return air from the conditioned area. This could be from air leaks in the return duct system drawing hot air from unconditioned areas.

The excessive load raises the suction pressure. The refrigerant is evaporating at a rate faster than the pumping rate of the compressor 105. If the system uses a TXV, the superheat will be normal to slightly high. The valve will operate at a higher flow rate to attempt to maintain superheat settings. If the system uses fixed metering devices, the superheat will be high. The fixed metering devices cannot feed enough increase in refrigerant quantity to keep the evaporator 110 fully active.

The high side or discharge pressure will be high. The compressor 105 will pump more vapor because of the increase in suction pressure. The condenser 107 must handle more heat and will develop a higher condensing temperature to eject the additional heat. A higher condensing temperature means a greater high side pressure. The quantity of liquid in the system has not changed, nor is the refrigerant flow restricted. The liquid subcooling will be in the normal range. The amperage draw of the unit will be high because of the additional load on the compressor 105.

When the temperature of the ambient air entering the condenser 107 is low, then the condenser 107 heat transfer rate is excessive, producing an excessively low discharge pressure. As a result, the suction pressure will be low because the amount of refrigerant through the metering device will be reduced. This reduction will reduce the amount of liquid refrigerant supplied to the evaporator 110. The coil will produce less vapor and the suction pressure drops.

The decrease in the refrigerant flow rate into the coil reduces the amount of active coil, and a higher superheat results. In addition, the reduced system capacity will decrease the amount of heat removed from the air. There will be higher temperature and relative humidity in the conditioned area and the high side pressure will be low. This starts a reduction in system capacity. The amount of subcooling of the liquid will be in the normal range. The quantity of liquid in the condenser 107 will be higher, but the heat transfer rate of the evaporator 110 is less. The amperage draw of the condensing unit will be less because the compressor 105 is doing less work.

The amount of drop in the condenser 107 ambient air temperature that the air conditioning system will tolerate depends on the type of pressure reducing device in the system. Systems using fixed metering devices will have a gradual reduction in capacity as the outside ambient drops from 95° F. This gradual reduction occurs down to 65° F. Below this temperature the capacity loss is drastic, and some means of maintaining head pressure must be employed to prevent the evaporator 110 temperature from dropping below freezing. Some systems control air through the condenser 107 via dampers in the airstream or a variable speed condenser 107 fan.

Systems that use TXV will maintain higher capacity down to an ambient temperature of 47° F. Below this temperature, controls must be used. The control of airflow through the condenser 107 using dampers or the condenser 107 fan speed control can also be used. In larger TXV systems, liquid quantity in the condenser 107 is used to control head pressure.

The higher the temperature of the air entering the condenser 107, the higher the condensing temperature of the refrigerant vapor to eject the heat in the vapor. The higher the condensing temperature, the higher the head pressure. The suction pressure will be high for two reasons: (1) the pumping efficiency of the compressor 105 will be less; and (2) the higher temperature of the liquid will increase the amount of flash gas in the metering device, further reducing the system efficiency.

The amount of superheat produced in the coil will be different in a TXV system and a fixed metering device system. In the TXV system the valve will maintain superheat close to the limits of its adjustment range even though the actual temperatures involved will be higher. In a fixed metering device system, the amount of superheat produced in the coil is the reverse of the temperature of the air through the condenser 107. The flow rate through the fixed metering devices are directly affected by the head pressure. The higher the air temperature, the higher the head pressure and the higher the flow rate. As a result of the higher flow rate, the subcooling is lower.

Table 2 shows the superheat that will be developed in a properly charged air conditioning system using fixed metering devices. The head pressure will be high at the higher ambient temperatures because of the higher condensing temperatures required. The condenser 107 liquid subcooling will be in the lower portion of the normal range. The amount of liquid refrigerant in the condenser 107 will be reduced slightly because more will stay in the vapor state to produce the higher pressure and condensing temperature. The amperage draw of the condensing unit will be high.

TABLE 2

| Air Temperature Entering Condenser 107 (° F.) | Superheat ° F. |
|---|---|
| 65 | 30 |
| 75 | 25 |
| 80 | 20 |
| 85 | 18 |
| 90 | 15 |
| 95 | 10 |
| 105 & above | 5 |

A shortage of refrigerant in the system means less liquid refrigerant in the evaporator 110 to pick up heat, and lower suction pressure. The smaller quantity of liquid supplied the evaporator 110 means less active surface in the coil for vaporizing the liquid refrigerant, and more surface to raise vapor temperature. The superheat will be high. There will be less vapor for the compressor 105 to handle and less head for the condenser 107 to reject, lower high side pressure, and lower condensing temperature. The compressor 105 in an air conditioning system is cooled primarily by the cool returning suction gas. Compressor 105s that are low on charge can have a much higher operating temperature.

The amount of subcooling will be below normal to none, depending on the amount of undercharge. The system operation is usually not affected very seriously until the subcooling is zero and hot gas starts to leave the condenser 107, together with the liquid refrigerant. The amperage draw of the condensing unit will be slightly less than normal.

An overcharge of refrigerant will affect the system in different ways, depending on the pressure reducing device used in the system and the amount of overcharge.

In system using a TXV, the valve will attempt to control the refrigerant flow in the coil to maintain the superheat setting of the valve. However, the extra refrigerant will back up into the condensing 107, occupying some of the heat transfer area that would otherwise be available for condensing. As a result, the discharge pressure will be slightly higher than normal, the liquid subcooling will be high, and the unit amperage draw will be high. The suction pressure and evaporator 110 superheat will be normal. Excessive overcharging will cause even higher head pressure, and hunting of the TXV.

For TXV systems with excessive overcharge the suction pressure will typically be high. Not only does the reduction in compressor 105 capacity (due to higher head pressure) raise the suction pressure, but the higher pressure will cause the TXV valve to overfeed on its opening stroke. This will cause a wider range of hunting of the valve. The evaporator 110 superheat will be very erratic from the low normal range to liquid out of the coil. The high side or discharge pressure will be extremely high. Subcooling of the liquid will also be high because of the excessive liquid in the condenser 107. The condensing unit amperage draw will be higher because of the extreme load on the compressor 105 motor.

The amount of refrigerant in the fixed metering system has a direct effect on system performance. An overcharge has a greater effect than an undercharge, but both affect system performance, efficiency (EER), and operating cost.

Figure 12:
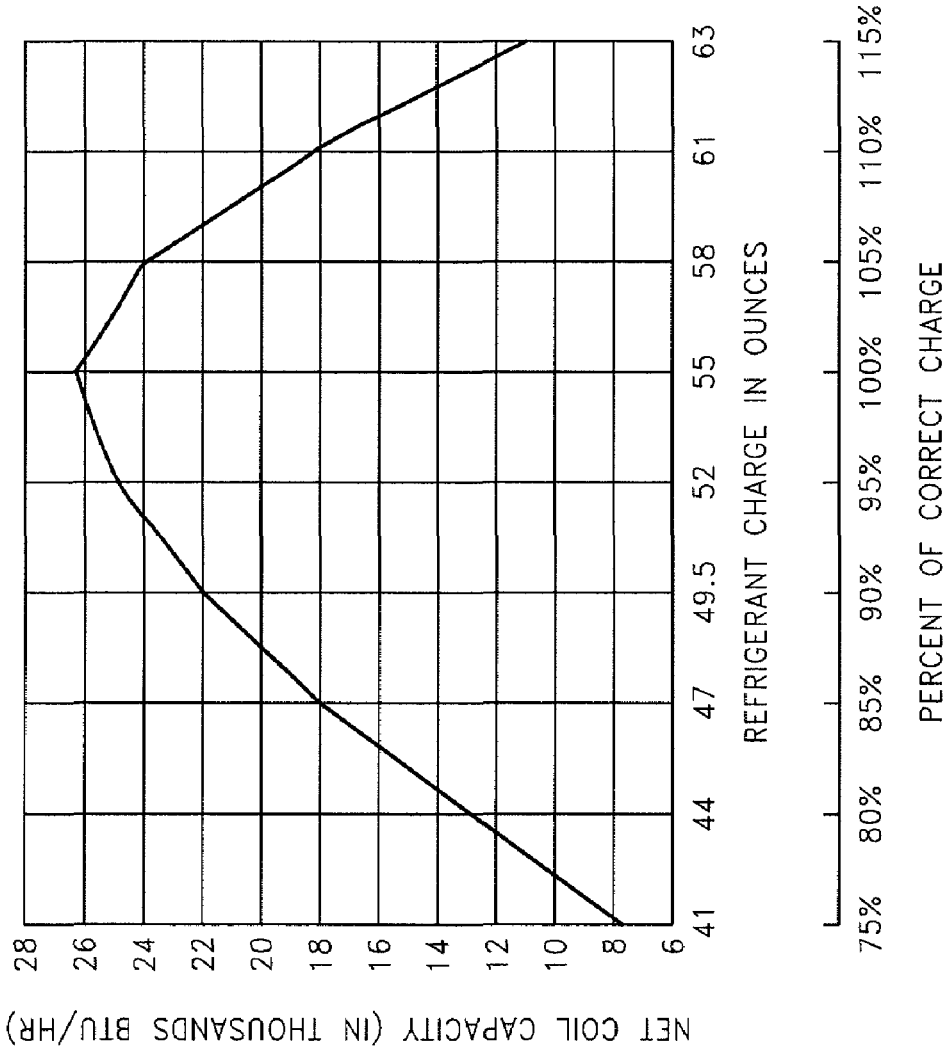
FIG. 12 shows heat capacity of a typical refrigerant-cycle system as a function of refrigerant charge.
Figure 13:
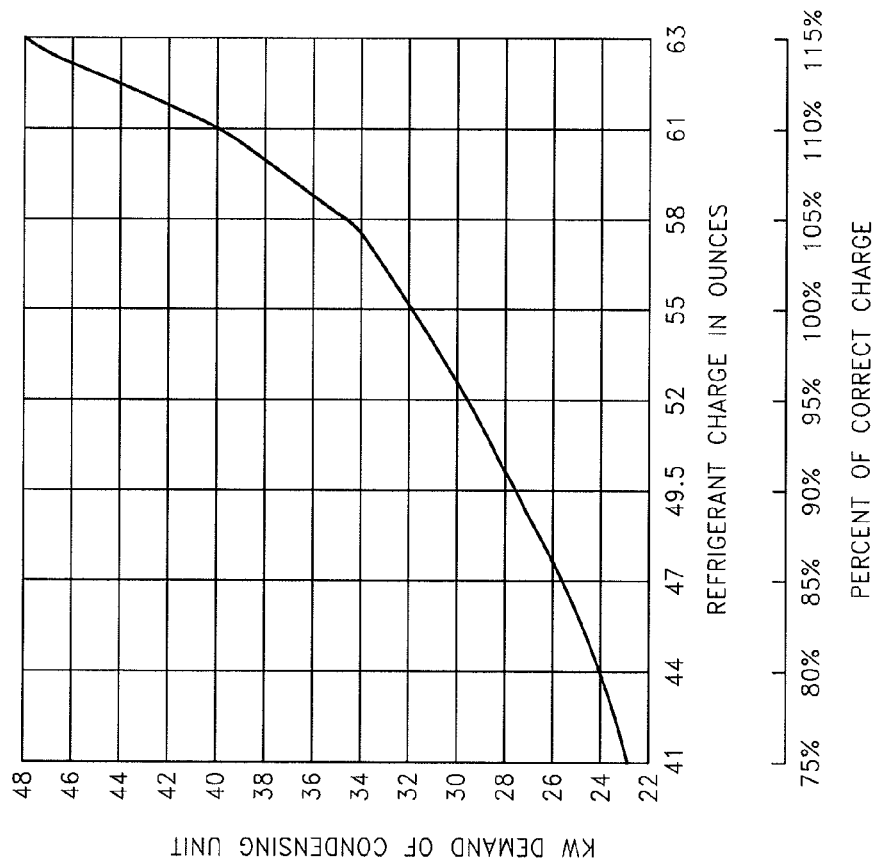
FIG. 13 shows power consumed in a typical refrigerant-cycle system as a function of refrigerant charge.
Figure 14:
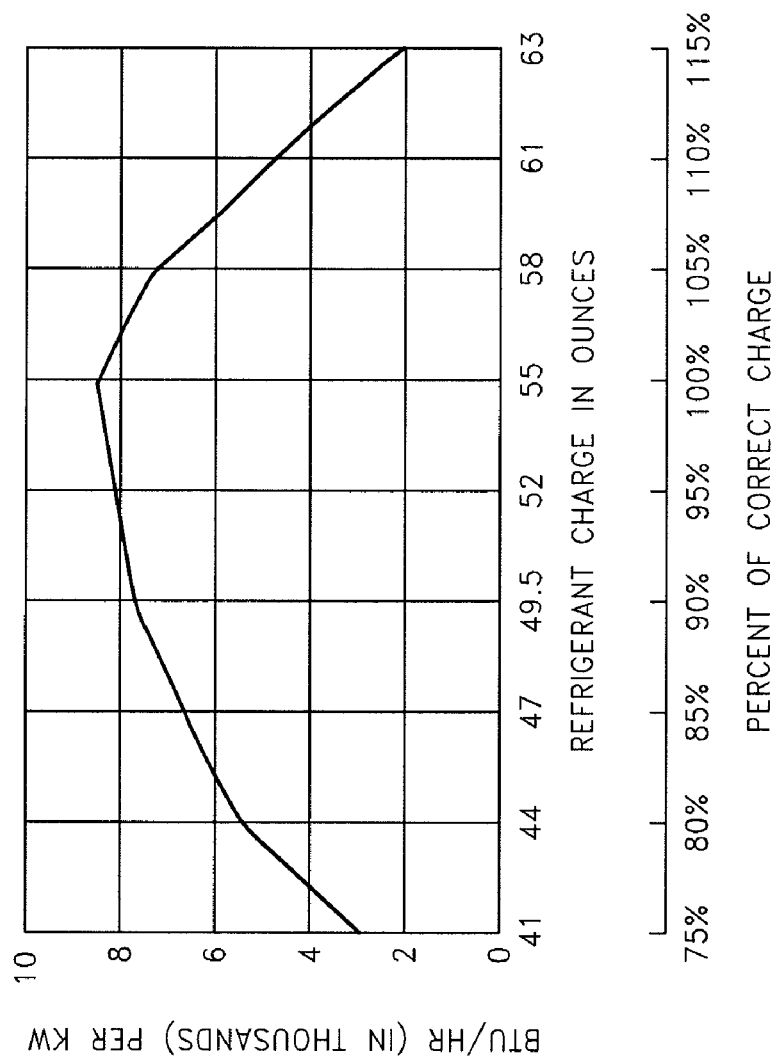
FIG. 14 shows efficiency of a typical refrigerant-cycle system as a function of refrigerant charge.

FIGS. 12 through 14 show how the performance of a typical capillary tube air conditioning system is affected by an incorrect amount of refrigerant charge. In FIG. 12, at 100% of correct charge (55 oz), the unit develops a net capacity of 26,200 Btu/hr. When the amount of charge is varied 5% in either direction, the capacity drops as the charge varied. Removing 5% (3 oz) of refrigerant reduces the net capacity to 25,000 Btu/hr. Another 5% (2.5 oz) reduces the capacity to 22,000 Btu/hr. From there on the reduction in capacity became very drastic: 85% (8 oz), 18,000 Btu/hr; 80% (11 oz), 13,000 Btu/hr; and 75% (14 oz), 8000 Btu/hr.

Overcharge has a similar effect but at a greater reduction rate. The addition of 3 oz of refrigerant (5%) reduces the net capacity to 24,600 Btu/hr; 6 oz added (10%) reduces the capacity to 19,000 Btu/hr; and 8 oz added (15%) drops the capacity to 11,000 Btu/hr. This shows that overcharging of a unit has a greater effect per ounce of refrigerant than does undercharging.

FIG. 13 is a chart showing the amount of electrical energy the unit demand because of pressure created by the amount of refrigerant in the system as the refrigerant charge is varied. At 100% of charge (55 oz) the unit uses 32 kW. As the charge is reduced, the wattage demand also drops, to 29.6 kW at 95% (3 oz), to 27.6 kW at 90% (6.5 oz), to 25.7 kW at 85% (8 oz), to 25 kW at 80% (11 oz), and to 22.4 kW at 75% (14 oz short of correct charge). When the unit is overcharged, the power consumed also increases. At 3 oz (5% overcharge) the power consumed is 34.2 kW, at 6 oz (10% overcharge) 39.5 kW, and at 8 oz (15% overcharge), 48 kW.

FIG. 14 shows the efficiency of the unit (EER rating) based on the Btu/hr capacity of the system versus the power consumed by the condensing unit. At correct charge (55 oz) the efficiency (EER rating) of the unit is 8.49. As the refrigerant is reduced, the EER rating drops to 8.22 at 9% of charge, to 7.97 at 90%, to 7.03 at 85%, to 5.2 at 80%, and to 3.57 at 75% of full refrigerant charge. When refrigerant is added, at 5% (3 oz) the EER rating drops to 7.19. At 10% (6 oz) the EER is 4.8, and at 15% overcharge (8 oz) the EER is 2.29.

The effect of overcharge produces a high suction pressure because the refrigerant flow to the evaporator 110 increases. Suction superheat decreases because of the additional quantity to the evaporator 110. At approximately 8 to 10% of overcharge, the suction superheat becomes zero and liquid refrigerant will leave the evaporator 110. This causes flooding of the compressor 105 and greatly increases the chance of compressor 105 failure. The high side or discharge pressure is high because of the extra refrigerant in the condenser 107. Liquid subcooling is also high for the same reason. The power draw increases due to the greater amount of vapor pumped as well as the higher compressor 105 discharge pressure.

Restrictions in the liquid line 108 reduce the amount of refrigerant to the pressure reducing device 109. Both TXV valve systems and fixed metering device systems will then operate with reduced refrigerant flow rate to the evaporator 110. The following observations can be made of liquid line 108 restrictions. First, the suction pressure will be low because of the reduced amount of refrigerant to the evaporator 110. The suction superheat will be high because of the reduced active portion of the coil, allowing more coil surface for increasing the vapor temperature as well as reducing the refrigerant boiling point. The high side or discharge pressure will be low because of the reduced load on the compressor 105. Liquid subcooling will be high. The liquid refrigerant will accumulate in the condenser 107. It cannot flow out at the proper rate because of the restriction. As a result, the liquid will cool more than desired. Finally, the amperage draw of the condensing unit will be low.

Either a plugged fixed metering device or plugged feeder tube between the TXV valve distributor and the coil will cause part of the coil to be inactive. The system will then be operating with an undersized coil, resulting in low suction pressure because the coil capacity has been reduced. The suction superheat will be high in the fixed metering device systems. The reduced amount of vapor produced in the coil and resultant reduction in suction pressure will reduce compressor 105 capacity, head pressure, and the flow rate of the remaining active capillary tubes. The high side or discharge pressure will be low.

Liquid subcooling will be high; the liquid refrigerant will accumulate in the condenser 107. The unit amperage draw will be low.

In TXV systems, a plugged feeder tube reduces the capacity of the coil. The coil cannot provide enough vapor to satisfy the pumping capacity of the compressor 105 and the suction pressure balances out at a low pressure. The superheat, however, will be in the normal range because the valve will adjust to the lower operating conditions and maintain the setting superheat range. The high side or discharge pressure will be low because of the reduced load on the compressor 105 and condenser 107.

Low suction and discharge pressure indicate a refrigerant shortage. The liquid subcooling is normal to slightly above normal. This indicates a surplus of refrigerant in the condenser 107. Most of the refrigerant is in the coil, where the evaporation rate is low due to the higher operating pressure in the coil. The amperage draw of the condensing unit would be low because of the light load on the compressor 105.

If the hot gas line 106 is restricted, then the high side or compressor 105 discharge pressure will be high if measured at the compressor 105 outlet or low if measured at the condenser 107 outlet or liquid line. In either case, the compressor 105 current draw will be high. The suction pressure is high due to reduced pumping capacity of the compressor 105. The evaporator 110 superheat is high because the suction pressure is high. The high side pressure is high when measured at the compressor 105 discharge or low when measured at the liquid line. Liquid subcooling is in the high end of the normal range. Even with all of this, the compressor 105 amperage draw is above normal. All symptoms point to an extreme restriction in the hot gas line 106. This problem is easily found when the discharge pressure is measured at the compressor 105 discharge.

When the measuring point is the liquid line 108 at the condenser 107 outlet, the facts are easily misinterpreted. High suction pressure and low discharge pressure will usually be interpreted as an inefficient compressor 105. The amperage draw of the compressor 105 must be measured. The high amperage draw indicates that the compressor 105 is operating against a high discharge pressure. A restriction apparently exists between the outlet of the compressor 105 and the pressure measuring point.

When the compressor 105 will not pump the required amount of refrigerant vapor (e.g., because it is undersized, or is not working at rated capacity). The suction pressure will balance out higher than normal. The evaporator 110 superheat will be high. The high side or discharge pressure will be extremely low. Liquid subcooling will be low because not much heat will be in the condenser 107. The condensing temperature will therefore be close to the entering air temperature. The amperage draw of the condensing unit will be extremely low, indicating that the compressor 105 is doing very little work.

The following formulas can be used by the systems 900, 1000 to calculate various operating parameters of the refrigerant-cycle system 100 using data from one or more of the sensors shown in FIG. 10.

Power is:

$$\text{Watts}=\text{volts}\times\text{amps}\times PF$$

where PF is the power factor.

Heat is:

$$Btu=W\times\Delta T$$

Specific heat is:

$$Btu=W\times c\times\Delta T$$

Sensible heat added or removed from a substance is:

$$Q=W\times SH\times\Delta T$$

Latent heat added or removed from a substance is:

$$Q=W\times LH$$

The refrigeration effect is:

$$W=\frac{200}{NRE}$$

where W weight of refrigerant circulated per minute (e.g., lb/min), 200 Btu/min is the equivalent of 1 ton of refrigeration, and NRE is the net refrigerating effect (Btu/lb of refrigerant)

The coefficient of performance (COP) is:

$$COP=\frac{\text{refrigerating\_effect}}{\text{heat\_of\_compression}}$$

System capacity is:

$$Q_t=4.45\times CFM\times\Delta h$$

where $Q_t$ is the total (sensible and latent) cooling being done, CFM is the airflow across the evaporator 110, and $\Delta h$ is the change of enthalpy of the air across the coil Condensing temperature is:

$$RCT=EAT+\text{split}$$

where RCT is the refrigerant condensing temperature, EAT is the temperature of the air entering the condenser 107, and split is the design temperature difference between the entering air temperature and the condensing temperatures of the hot high-pressure vapor from the compressor 105

Net cooling capacity is:

$$HC=HT-HM$$

where HT is the heat transfer (gross capacity), HM is the motor heat, HC is the net cooling capacity, and PF is the power factor.

Airflow rate of a system can be expressed as:

$$Q=Q_s(1.08\times TD)$$

where Q is the flow rate in CFM, $Q_s$ is the sensible-heat load in But/hr, and TD is the dry bulb temperature difference in ° F.

In a fan, airflow (CFM) is approximately related to rotation (rpm) as follows:

$$\frac{CFM_2}{CFM_1}=\frac{rpm_2}{rpm_1}$$

In a fan, pressure is approximately related to rotation as follows:

$$\frac{SP_2}{SP_1}=\left(\frac{rpm_2}{rpm_1}\right)^2$$

In a fan, work is approximately related to rotation as follows:

$$\frac{Bhp_2}{Bhp_1}=\left(\frac{rpm_2}{rpm_1}\right)^3$$

In one embodiment, the tachometer 1033 is provided to measure the rotational velocity of the fan 123. In one embodiment, the tachometer 1032 is provided to measure the rotational velocity of the fan 122. In one embodiment, the system 1000 uses one or more of the above fan equations to calculate desired fan rotation rates. In one embodiment, the system 1000 controls the speed of the fan 123 and/or the fan 122 to increase system efficiency.

The quantity of air used for cooling, based on the sensible cooling is approximately:

$$CFM=H_s/(TD\times 1.08)$$

The sensible heat removed is $$Q_s=1.08\times CFM\times DBT\text{ difference}$$

The latent heat removed is:

$$Q_l=0.68\times CFM\times gr\text{ moisture difference}$$

The total heat removed is:

$$Q_t=Q_s+Q_l$$

or $$Q_t=4.5\times CFM\times\text{total heat difference}$$

The rate of heat transfer is:

$$Q_t=U\times A\times TD$$

where Q is the heat transfer (Btuh), U is the overall heat transfer coefficient (Btuh/Ft$^2$/° F.), A is the area (ft$^2$), TD is the temperature difference between inside and outside design temperature and the refrigerated space design temperature.

The keypad 1050 is used to provide control inputs to the efficiency monitoring system. The display 1008 provides feedback to the user, temperature set point display. In one embodiment, the power use and/or power cost can be displayed on the display 1008. In one embodiment, the system 1000 receives rate information from the power company to use in calculating power costs. In one embodiment, the absolute efficiency of the refrigerant-cycle system can be shown on the display 1008. In one embodiment, the relative efficiency of the refrigerant-cycle system can be shown on the display 1008. In one embodiment, the data from various sensors in the system 1000 can be shown on the display 1008. In one embodiment, diagnostic messages (e.g., change the filter, add refrigerant, etc.) are shown on the display 1008. In one embodiment, messages from the power company are shown on the display 1008. In one embodiment, warning messages from the power company are shown on the display 1008. In one embodiment, the thermostat 1001 communicates with the power company (or other remote device) using power line communication methods such as, for example, BPL.

Then the system 1000 is configured, the installer programs in the fixed system parameters needed for calculation of efficiency and/or other quantities derived from the sensor data. Typical fixed programmed parameters include the type of refrigerant, the compressor specifications, the condenser specifications, the evaporator specifications, the duct specifications, the fan specifications, the system SEER, and/or other system parameters. Typical fixed programmed parameters can also include equipment model and/or serial numbers, manufacturer data, engineering data, etc.

In one embodiment, the system 1000 is configured by bringing the refrigerant-cycle system up to design specifications, and then running the system 1000 in a calibration mode wherein the system 1000 takes sensor readings to measure normal baseline parameters for the refrigerant-cycle system. Using the measured baseline data, the system 1000 can calculate various system parameters (e.g., split temperatures, etc.).

In one embodiment, the system 1000 is first run in a calibration mode to measure baseline data, and then run in a normal monitoring mode wherein it compares operation of the refrigerant-cycle system with the baseline data. The system 1000 then gives alerts to potential problems when the operating parameters vary too much from the baseline data.

In one embodiment, the system 1000 is configured by using a combination of programmed parameters (e.g., refrigerant type, temperature splits, etc.) and baseline data obtained by operating the refrigerant-cycle system.

Figure 15:
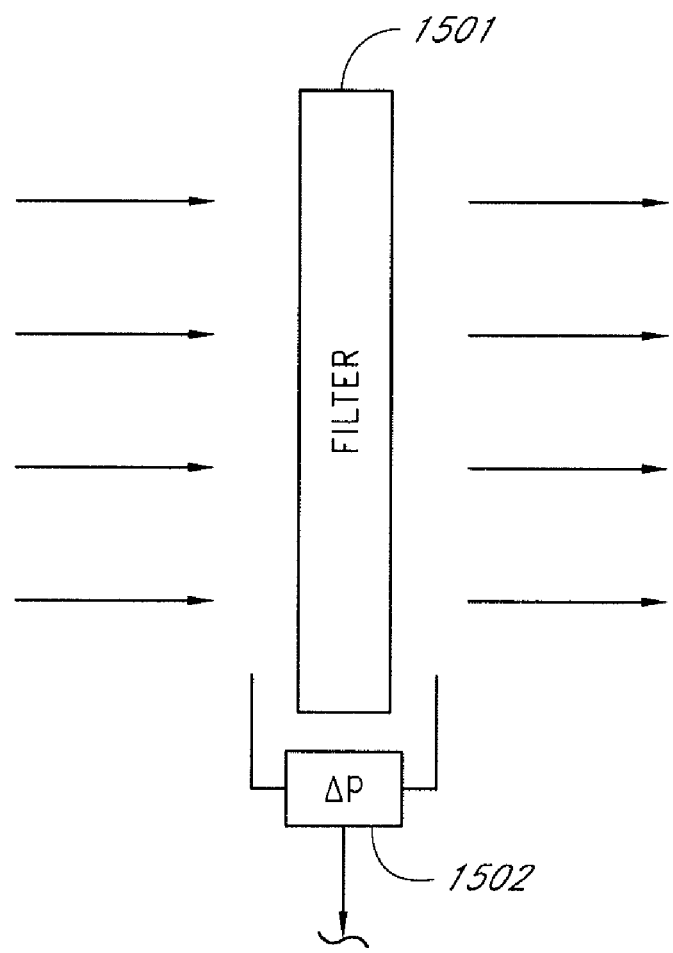
FIG. 15 shows a differential-pressure sensor used to monitor an air filter in an air-handler system.

FIG. 15 shows a differential-pressure sensor 1502 used to monitor an air filter 1501 in an air-handler system. As the filter becomes clogged, the differential pressure across the filter will rise. This increase in differential pressure is measured by the differential pressure sensor 1502. The differential pressure measured by the differential pressure sensor 1502 is used to assess the state of the filter 1501. When the differential pressure is too high, then replacement of the filter 1501 is indicated.

Figure 16:
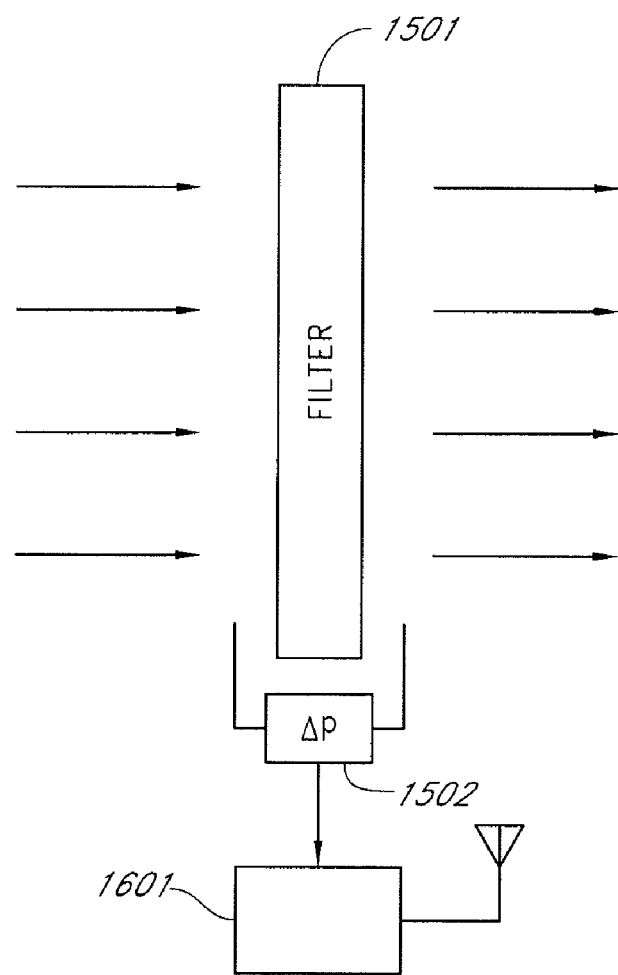
FIG. 16 shows a differential-pressure sensor used to monitor an air filter in an air-handler system using a wireless system to provide filter differential pressure data back to other aspects of the monitoring system.

FIG. 16 shows the differential-pressure sensor 1502 from FIG. 15 provided to a wireless communication unit to allow the data from the differential pressure sensor 1502 to be provided to other aspects of the monitoring system, such as, for example, the condenser unit sender 1002 or the thermostat 1001.

Figure 17:
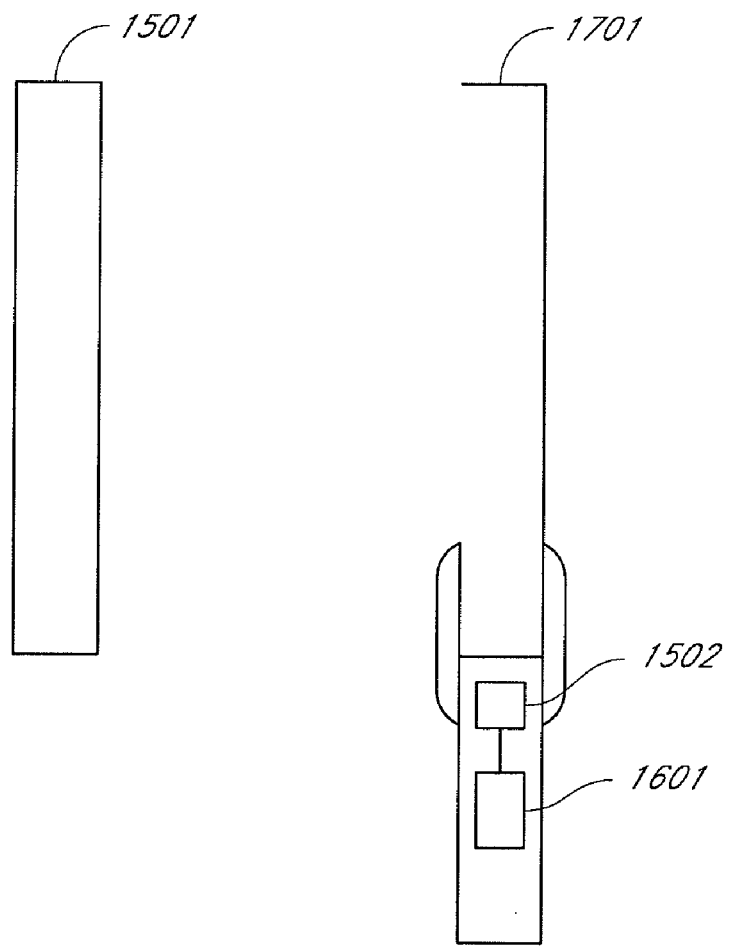
FIG. 17 shows the system of FIG. 16 implemented using a filter frame to facilitate retrofitting of existing air handler systems.

FIG. 17 shows the system of FIG. 16 implemented using a filter frame 1701 to facilitate retrofitting of existing air handler systems. The frame 1701 includes the sensor 1502 and the sender 1601. The frame 1701 is configured to fit into a standard filter frame. The frame 1701 is configured to hold a standard filter 1501. In one embodiment, the frame 1701 evaluates the cleanliness of the filter 1501 by measuring a differential pressure between the filter input and output air. In one embodiment, the frame 1701 evaluates the cleanliness of the filter 1501 by providing a source of light on one side of the filter, a light sensor on the other side of the filter, and by measuring the light transmission through the filter. In one embodiment, the frame 1701 is calibrated to a baseline light transmission level. In one embodiment, the frame 1701 signals that the filter is dirty when the light transmission falls below a fixed threshold level. In one embodiment, the frame 1701 calibrates a baseline light transmission level each time a clean filter is installed. In one embodiment, the frame 1701 signals that the filter is dirty when the light transmission falls below a percentage of the baseline level.

Although various embodiments have been described above, other embodiments will be within the skill of one of ordinary skill in the art. Thus, for example, although described primarily in terms of an air-conditioning system, one of ordinary skill in the art will recognize that all or part of the system 1000 can be applied to other refrigerant-cycle systems, such as, for example, commercial HVAC systems, refrigerator systems, freezers, water chillers, etc. Thus, the invention is limited only by the claims that follow.

What is claimed is:

1. An intelligent thermostat for monitoring the operation of a refrigerant-cycle system, comprising:
   a display configured to display temperature and system efficiency; and
   a processing system configured to receive sensor data from one or more condenser unit sensors and one or more evaporator unit sensors, said processing system configured to calculate an efficiency of said refrigerant-cycle system using at least a portion of said sensor data from said one or more condenser unit sensors and at least a portion of said sensor data from said one or more evaporator unit sensors, and to display a parameter related to said efficiency, wherein said processing system is configured to diagnose performance problems due to excessive load using at least a portion of said sensor data from said one or more condenser unit sensors and at least a portion of said sensor data from said one or more evaporator unit sensors, wherein said efficiency comprises an actual efficiency based at least in part on an ambient temperature.

2. The intelligent thermostat of claim 1, wherein said processing system is configured to calculate and display an energy cost of using said refrigerant-cycle system.

3. The intelligent thermostat of claim 1, wherein said processing system is configured to calculate and display energy usage of said refrigerant-cycle system.

4. The intelligent thermostat of claim 1, wherein said processing system is configured to diagnose performance problems due to refrigerant overcharge.

5. The intelligent thermostat of claim 1, wherein said processing system is configured to diagnose performance problems due to liquid line restriction.

6. The intelligent thermostat of claim 1, wherein said processing system is configured to identify performance problems due to suction line restriction.

7. The intelligent thermostat of claim 1, wherein said processing system is configured to identify performance problems due to hot gas line restriction.

8. The intelligent thermostat of claim 1, wherein said processing system is configured to identify performance problems due to inefficient compressor operation.

9. The intelligent thermostat of claim 1, wherein said processing system is configured to provide data for plots of energy usage and costs.

10. The intelligent thermostat of claim 1, wherein said processing system is configured to provide data related to operation of said refrigerant-cycle system to a remote monitoring center.

11. The intelligent thermostat of claim 1, wherein said processing system is configured to provide data related to operation of said refrigerant-cycle system to a remote monitoring center using power line networking.

12. The intelligent thermostat of claim 1, wherein said processing system is configured to provide data related to operation of said refrigerant-cycle system to a remote monitoring center using broadband over powerline networking.

13. The intelligent thermostat of claim 1, further comprising an electronically-controlled metering device to allow control of refrigerant into an evaporator in an energy-efficient matter.

14. The intelligent thermostat of claim 1, wherein said intelligent thermostat is configured with data regarding a maximum expected efficiency for the refrigerant-cycle system.

15. The intelligent thermostat of claim 1, wherein said intelligent thermostat is configured with data regarding a type of refrigerant used in the refrigerant-cycle system.

16. The intelligent thermostat of claim 1, wherein said intelligent thermostat is configured with data regarding the characteristics of the condenser.

17. The intelligent thermostat of claim 1, wherein said intelligent thermostat is configured with data regarding the characteristics of the evaporator.

18. The intelligent thermostat of claim 1, wherein said condenser unit sensors comprise a temperature sensor configured to measure a temperature of the refrigerant in a suction line.

19. The intelligent thermostat of claim 1, wherein said condenser unit sensors comprise a temperature sensor configured to measure a temperature of the refrigerant in a liquid line.

20. The intelligent thermostat of claim 1, wherein said condenser unit sensors comprise a temperature sensor configured to measure a temperature of the refrigerant in a hot gas line.

21. The intelligent thermostat of claim 1, wherein said condenser unit sensors comprise a pressure sensor configured to measure a pressure of the refrigerant in a suction line.

22. The intelligent thermostat of claim 1, wherein said condenser unit sensors comprise a pressure sensor configured to measure a pressure of the refrigerant in a liquid line.

23. The intelligent thermostat of claim 1, wherein said condenser unit sensors comprises a pressure sensor configured to measure a pressure of the refrigerant in a hot gas line.

24. The intelligent thermostat of claim 1, wherein said condenser unit sensors comprise at least one refrigerant flow sensor.

25. The intelligent thermostat of claim 1, wherein said condenser unit sensors comprise at least one refrigerant contaminant sensor.

26. The intelligent thermostat of claim 1, wherein said condenser unit sensors comprises at least one condenser fan tachometer.

27. The intelligent thermostat of claim 1, wherein said condenser unit sensors comprise at least one temperature sensor configured to measure a temperature of air out of said condenser.

28. The intelligent thermostat of claim 1, wherein said evaporator unit sensors comprise a temperature sensor to measure a temperature of refrigerant into said evaporator.

29. The intelligent thermostat of claim 1, wherein said evaporator unit sensors comprise a temperature sensor to measure a temperature of refrigerant out of said evaporator.

30. The intelligent thermostat of claim 1, wherein said evaporator unit sensors comprise a temperature sensor to measure a temperature of air into said evaporator.

31. The intelligent thermostat of claim 1, wherein said evaporator unit sensors comprise a temperature sensor to measure a temperature of air out of said evaporator.

32. The intelligent thermostat of claim 1, wherein said evaporator unit sensors comprise at least one humidity sensor.

33. The intelligent thermostat of claim 1, wherein said evaporator unit sensors comprise at least one air flow sensor.

34. The intelligent thermostat of claim 1, wherein said evaporator unit sensors comprise at least one differential pressure sensor.

35. The intelligent thermostat of claim 1, further comprising a modem, said intelligent thermostat configured to report performance criteria to a monitoring system using said modem.

36. The intelligent thermostat of claim 1, further comprising a modem, said intelligent thermostat configured to receive shutdown instructions using said modem.

37. The intelligent thermostat of claim 1, further comprising a modem, said intelligent thermostat configured to receive commands using said modem.

38. The intelligent thermostat of claim 1, further comprising a modem, said intelligent thermostat configured to receive operating instructions using said modem.

* * * * *

UNITED STATES PATENT AND TRADEMARK OFFICE
CERTIFICATE OF CORRECTION

PATENT NO. : 7,343,751 B2
APPLICATION NO. : 11/417609
DATED : March 18, 2008
INVENTOR(S) : Lawrence Kates It is certified that error appears in the above-identified patent and that said Letters Patent is hereby corrected as shown below:

At page 2, column 2 (U.S. Patent Documents), line 7, please delete "Strierner" and insert -- Striemer --, therefor.

At page 2, column 2 (Other Publications), line 23, please delete "cataog" and insert -- catalog --, therefor.

At sheet 2 of 25 (Below Refrigerant) (FIG. 2), line 2, after "ENTROPY in", please delete "Btu/(lb)(°R)" and insert -- Btu/(lb)(°F) --, therefor.

At sheet 5 of 25 (Below Heat of Compression) (FIG. 5), line 1, please delete "hd-he" and insert -- hd-hc' --, therefor.

At sheet 5 of 25 (Below Evaporating Temperature) (FIG. 5), line 1, please delete "NRE=hc-ha" and insert -- hc'-ha --, therefor.

At sheet 6 of 25 (Below Superheat) (FIG. 6), line 1, please delete "hd-he" and insert -- hd'-he' --, therefor.

Signed and Sealed this

Fourth Day of November, 2008

JON W. DUDAS
*Director of the United States Patent and Trademark Office*